US008968343B2

(12) United States Patent
Funamura et al.

(10) Patent No.: US 8,968,343 B2
(45) Date of Patent: Mar. 3, 2015

(54) PUNCTURING NEEDLE ASSISTING TOOL

(75) Inventors: Shigeaki Funamura, Fukuroi (JP); Hisataka Harada, Fukuroi (JP); Satoru Igarashi, Tokyo (JP); Kazuhiro Abe, Fukuroi (JP)

(73) Assignee: Covidien LP, Mansfield, MA (US)

( * ) Notice: Subject to any disclaimer, the term of this patent is extended or adjusted under 35 U.S.C. 154(b) by 68 days.

(21) Appl. No.: 12/487,108

(22) Filed: Jun. 18, 2009

(65) Prior Publication Data

US 2009/0318939 A1 Dec. 24, 2009

(30) Foreign Application Priority Data

Jun. 24, 2008 (JP) ................... 2008-164032

(51) Int. Cl.
*A61B 17/04* (2006.01)
*A61B 17/06* (2006.01)
*A61B 19/02* (2006.01)

(52) U.S. Cl.
CPC ......... *A61B 17/0482* (2013.01); *A61B 17/0485* (2013.01); *A61B 17/06061* (2013.01); *A61B 17/0469* (2013.01); *A61B 2017/06052* (2013.01); *A61B 2019/0258* (2013.01)
USPC ........................................ 606/148

(58) Field of Classification Search
CPC .......... A61M 25/02; A61M 2025/024; A61M 2025/0246; A61M 5/1418; A61B 17/0482; A61B 2017/0472
USPC ................. 606/129, 130, 139, 144–148, 232; 604/170.02, 174, 177–179, 192; 206/366; 24/326–368, 542, 543; 248/221.11–222.13, 223.31–224.61, 248/229.1–229.26, 67.7, 68.1, 74.1, 74.4; 215/224, 225, 235–245

See application file for complete search history.

(56) References Cited

U.S. PATENT DOCUMENTS 2,012,776 A  8/1935  Roeder
4,775,121 A * 10/1988  Carty ........................ 248/68.1
4,935,027 A  6/1990  Yoon (Continued)

FOREIGN PATENT DOCUMENTS

DE   2900265 A1   9/1980
EP   1844718 A1  10/2007

(Continued)

OTHER PUBLICATIONS

European Search Report for EP 09008041.7 dated Sep. 23, 2009, 6 pgs.

(Continued)

*Primary Examiner* — Katherine M Shi

(57) ABSTRACT

A puncturing needle assisting tool. A first rotating portion 122 rotates from an open to a closed position, around a first hinge connecting portion 126 as the rotating center, to the surface side of an assisting tool main unit 112 to close the surface opening of a first guide groove 116a. A second rotating portion 124 rotates from an open position to a closed position, around a second hinge connecting portion 128 as the rotating center, to the surface side of an assisting tool main unit 112 to close the surface openings of second guide grooves 116b through 116d. The puncturing needles move along the guide grooves to puncture into the body in a proper state, without shifting. Locking protrusions 134, 130 maintain the closed positions of the first and second rotating portions 122, 124 respectively.

7 Claims, 26 Drawing Sheets

(56) References Cited

U.S. PATENT DOCUMENTS

| | | | |
|---|---|---|---|
| 5,037,433 A | 8/1991 | Wilk et al. | |
| 5,052,396 A | 10/1991 | Wedel et al. | |
| 5,100,387 A | 3/1992 | Ng | |
| 5,123,914 A | 6/1992 | Cope | |
| 5,226,892 A * | 7/1993 | Boswell | 604/180 |
| 5,242,427 A | 9/1993 | Bilweis | |
| 5,251,873 A | 10/1993 | Atkinson et al. | |
| 5,281,237 A | 1/1994 | Gimpelson | |
| 5,330,488 A | 7/1994 | Goldrath | |
| 5,336,229 A | 8/1994 | Noda | |
| 5,336,231 A | 8/1994 | Adair | |
| 5,363,539 A * | 11/1994 | Tisol | 24/543 |
| 5,364,410 A | 11/1994 | Failla et al. | |
| 5,389,082 A | 2/1995 | Baugues et al. | |
| 5,391,182 A | 2/1995 | Chin | |
| 5,462,560 A | 10/1995 | Stevens | |
| 5,499,991 A | 3/1996 | Garman et al. | |
| 5,501,691 A | 3/1996 | Goldrath | |
| 5,531,699 A | 7/1996 | Tomba et al. | |
| 5,562,684 A | 10/1996 | Kammerer | |
| 5,569,269 A | 10/1996 | Hart et al. | |
| 5,626,590 A | 5/1997 | Wilk | |
| 5,643,295 A | 7/1997 | Yoon | |
| 5,653,411 A * | 8/1997 | Picco et al. | 248/74.1 |
| 5,653,716 A | 8/1997 | Malo et al. | |
| 5,665,096 A | 9/1997 | Yoon | |
| 5,681,333 A | 10/1997 | Burkhart et al. | |
| 5,722,981 A | 3/1998 | Stevens | |
| 5,728,109 A | 3/1998 | Schulze et al. | |
| 5,741,276 A | 4/1998 | Poloyko et al. | |
| 5,782,845 A | 7/1998 | Shewchuk | |
| 5,795,335 A * | 8/1998 | Zinreich | 604/174 |
| 5,817,108 A | 10/1998 | Poncet | |
| 5,817,111 A | 10/1998 | Riza | |
| 5,895,395 A | 4/1999 | Yeung | |
| 5,897,563 A | 4/1999 | Yoon et al. | |
| 5,921,993 A | 7/1999 | Yoon | |
| 5,938,668 A | 8/1999 | Scirica et al. | |
| 6,022,360 A | 2/2000 | Reimels et al. | |
| 6,036,700 A | 3/2000 | Stefanchik et al. | |
| 6,066,146 A | 5/2000 | Carroll et al. | |
| 6,110,183 A | 8/2000 | Cope | |
| 6,113,068 A | 9/2000 | Ryan | |
| 6,113,611 A | 9/2000 | Allen et al. | |
| RE36,974 E | 11/2000 | Bonutti | |
| 6,156,056 A | 12/2000 | Kearns et al. | |
| 6,418,341 B1 | 7/2002 | Hofmann et al. | |
| 6,451,024 B1 | 9/2002 | Thompson et al. | |
| 6,500,184 B1 | 12/2002 | Chan et al. | |
| 6,524,317 B1 | 2/2003 | Ritchart et al. | |
| 6,629,534 B1 | 10/2003 | St. Goar et al. | |
| 6,638,286 B1 | 10/2003 | Burbank et al. | |
| 6,699,263 B2 | 3/2004 | Cope | |
| 7,090,690 B2 | 8/2006 | Foerster et al. | |
| 7,306,613 B2 | 12/2007 | Kawashima et al. | |
| 7,320,693 B2 | 1/2008 | Pollack et al. | |
| 7,731,726 B2 | 6/2010 | Belhe et al. | |
| 7,918,868 B2 | 4/2011 | Marshall et al. | |
| 2002/0147456 A1 | 10/2002 | Diduch et al. | |
| 2003/0004523 A1 | 1/2003 | Chan et al. | |
| 2003/0109883 A1 | 6/2003 | Matsuzaki et al. | |
| 2004/0122473 A1 | 6/2004 | Ewers et al. | |
| 2004/0249393 A1 | 12/2004 | Weisel et al. | |
| 2004/0249395 A1 | 12/2004 | Mikkaichi et al. | |
| 2005/0253033 A1 * | 11/2005 | Mizukoshi et al. | 248/229.23 |
| 2005/0288689 A1 | 12/2005 | Kammerer et al. | |
| 2006/0069398 A1 | 3/2006 | Suzuki et al. | |
| 2007/0018057 A1 * | 1/2007 | Kovac | 248/68.1 |
| 2007/0023305 A1 | 2/2007 | Chan et al. | |
| 2007/0118153 A1 | 5/2007 | Funamura et al. | |
| 2007/0179509 A1 | 8/2007 | Nagata et al. | |
| 2007/0282351 A1 | 12/2007 | Harada et al. | |
| 2007/0293876 A1 | 12/2007 | Abe et al. | |
| 2008/0200931 A1 | 8/2008 | Harada et al. | |
| 2008/0228204 A1 | 9/2008 | Hamilton et al. | |
| 2008/0243147 A1 | 10/2008 | Hamilton et al. | |
| 2008/0255591 A1 | 10/2008 | Harada et al. | |
| 2008/0269781 A1 | 10/2008 | Funamura et al. | |
| 2009/0163939 A1 | 6/2009 | Mabuchi et al. | |

FOREIGN PATENT DOCUMENTS

| | | |
|---|---|---|
| EP | 1961387 A2 | 8/2008 |
| JP | 61205510 U | 12/1986 |
| JP | 04226643 A | 8/1992 |
| JP | 05161655 A | 6/1993 |
| JP | 06024533 B2 | 4/1994 |
| JP | 06044511 U | 6/1994 |
| JP | 07328020 | 12/1995 |
| JP | 2002336262 A | 11/2002 |
| JP | 2004141646 A | 5/2004 |
| JP | 2005270332 A | 10/2005 |
| JP | 2006025932 | 2/2006 |
| JP | 2006025933 | 2/2006 |
| JP | 2006025934 | 2/2006 |
| JP | 2006151429 | 5/2006 |
| JP | 2007039175 A | 2/2007 |
| JP | 2008164032 A | 7/2008 |
| WO | 9421178 A1 | 9/1994 |
| WO | 9522932 A1 | 8/1995 |
| WO | 03065903 A1 | 8/2003 |
| WO | 2004006782 A1 | 1/2004 |
| WO | 2007018520 A1 | 2/2007 |

OTHER PUBLICATIONS

Office action dated Sep. 29, 2010 from U.S. Appl. No. 12/033,221; 7 pages.
Office action issued Apr. 25, 2012 in related U.S. Appl. No. 13/207,655, 5 pages.
Response to Office action filed Jul. 25, 2012 in related U.S. Appl. No. 13/207,655, 6 pages.
Advisory Action issued May 20, 2011 from related U.S. Appl. No. 12/033,221—3 pgs.
Supplemental Response filed Jun. 29, 2011 to Office Action issued Mar. 2, 2011 and Advisory Action issued May 20, 2011 regarding U.S. Appl. No. 12/033,221—7 pgs.
Office action issued Apr. 25, 2012 regarding U.S. Appl. No. 13/207,655—5 pgs.
Response filed Apr. 22, 2011 to Office Action dated Mar. 2, 2011 from related U.S. Appl. No. 12/033,221. 7 pgs.
Response filed Dec. 10, 2010 to Office Action dated Sep. 29, 2010 regarding U.S. Appl. No. 12/033,221; 7 pgs.
Office action issued Mar. 2, 2011 regarding U.S. Appl. No. 12/033,221; 6 pgs.

* cited by examiner (a)

(b)

(a)

(b)

(a)

(b)

PUNCTURING NEEDLE ASSISTING TOOL

FIELD OF THE INVENTION

The present invention generally relates to a puncturing needle assisting tool that is used when puncturing tissue with a plurality of puncturing needles and is used for securing an internal organ onto a skin side portion using surgical sutures.

BACKGROUND OF THE INVENTION

For individuals with reduced abilities to ingest food orally under their own power, due to advanced age or illness, gastric catheters are used to supply liquid diets, such as liquid foods or nutritional supplements, or the like, into the stomachs of the patients. A gastric catheter is attached by forming an opening portion in the abdomen of the patient. When attaching the gastric catheter, the abdominal wall and the gastric wall are secured together in advance using sutures. The technology for securing the gastric wall to the abdominal wall is well known in the prior art (see Japanese Patent Application 2008-164032, for example).

In this technology, holes are provided in an insertion length adjusting plate, into which a needle comprising a suture thread insertion needle and an outer needle for securing an internal organ, such as the gastric wall, to the abdominal wall can fit. A constant interval is maintained by connecting, via a connecting plate, the outer needle and the suture thread insertion needle. The insertion depth of each needle is adjusted to the via an insertion depth adjusting plate slidable in an axial direction of the needles. The needle puncturing operation is performed simultaneously with the joining together of the suture thread insertion needle and the outer needle. First, the outer needle and the suture thread insertion needle penetrate through the abdominal wall and gastric wall to puncture the gastric lumen. Then, an inner needle within the outer needle is slid inwards so that a snare loop at the tip of the inner needle protrudes, in a direction that is perpendicular to the axial direction of the needles and from a tip hole portion of the needle. On the other hand, a thread is introduced into the suture thread insertion needle, and the tip portion of the thread passes through the inside of the snare loop. Withdrawing the inner needle draws the snare loop into the outer needle. Following this, the inner needle is removed from the body, and with both ends of the thread extracted from the body, both the outer needle and the suture thread insertion needle are removed. The thread is tied by an operation of applying a tensile force to both ends of the thread, to cause the gastric wall to be in contact with the abdominal wall, thereby enabling a tight seal therebetween.

However, as seen in the prior art, two separate plates (the connecting plate and the insertion length adjusting plate) must be used. In addition, the outer needle and the suture thread insertion needle must each individually be fitted into the holes in those two plates, and thus the puncturing operations are inefficient.

SUMMARY OF THE INVENTION

Other objects and features will be in part apparent and in part pointed out hereinafter.

Figure 1:
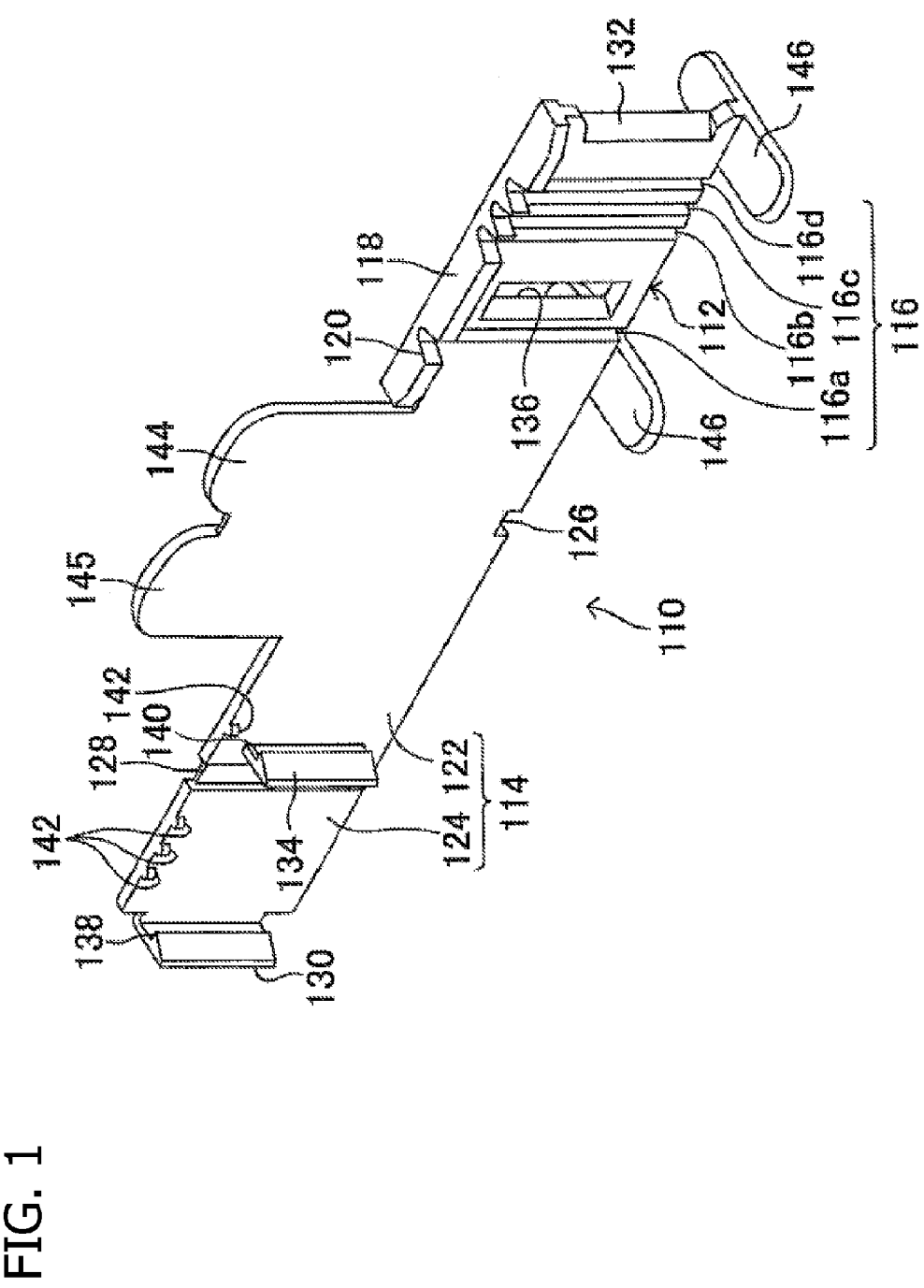
FIG. 1 is a perspective view of a front surface side of a puncturing needle assisting tool according to a first embodiment of the invention.

EXPLANATION OF REFERENCE CHARACTERS 110, 180, 210, 310, 410, 510: Puncturing Needle Assisting Tool
28: Suture thread
A: Abdominal Wall
B: Gastric Wall
21: Outer Insertion Puncturing Needle
30: Extraction Puncturing Needle
116: Guide Groove
116a: First Guide Groove
116b, 116c, 116d: Second Guide Groove
112, 512: Assisting Tool Main Unit
126, 426, 427, 526: First Hinge Connecting Portion
128: Second Hinge Connecting Portion
114, 414, 514: Rotating Member
130, 134, 182, 240, 334, 430, 531: Locking Protrusion
132: Locking Notch
136, 232, 336, 436, 537: Locking Hole
122, 422: First Rotating Portion
124, 424, 524: Second Rotating Portion
144, 145, 445a, 445b, 544, 545: Grip Portion Corresponding reference characters indicate corresponding parts throughout the drawings.

DESCRIPTION OF THE PREFERRED EMBODIMENTS

A first embodiment of a puncturing needle assisting tool as set forth in the present invention is explained based on FIG. 1 through FIG. 22. Note that in the first embodiment, the puncturing needle assisting tool is explained as that which is used when inserting a plurality of puncturing needles into the gastric wall side from the abdominal wall side in order to secure, using surgical sutures, the gastric wall of the stomach (generally the internal organ) to the abdominal wall (generally the skin-side portion).

Figure 2:
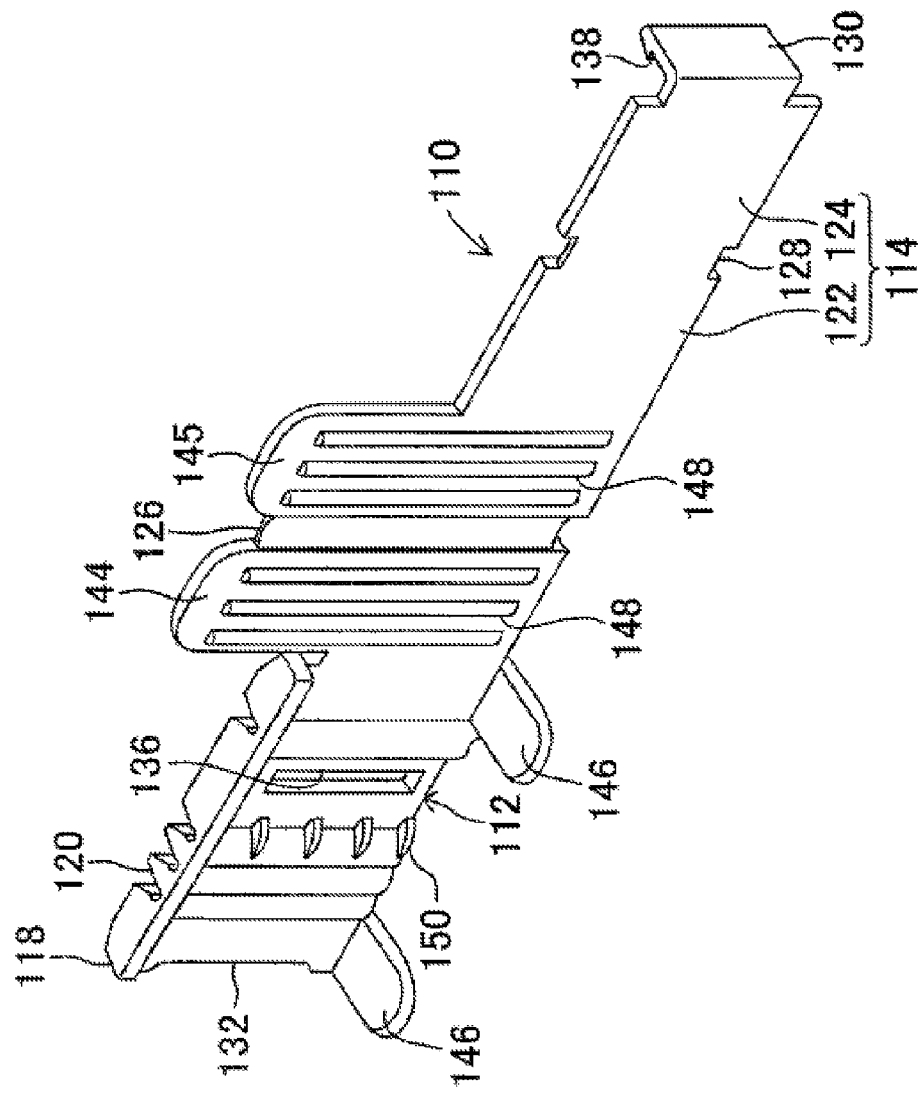
FIG. 2 is a perspective view of a back surface side of the puncturing needle assisting tool according to the first embodiment of the invention.
Figure 3:
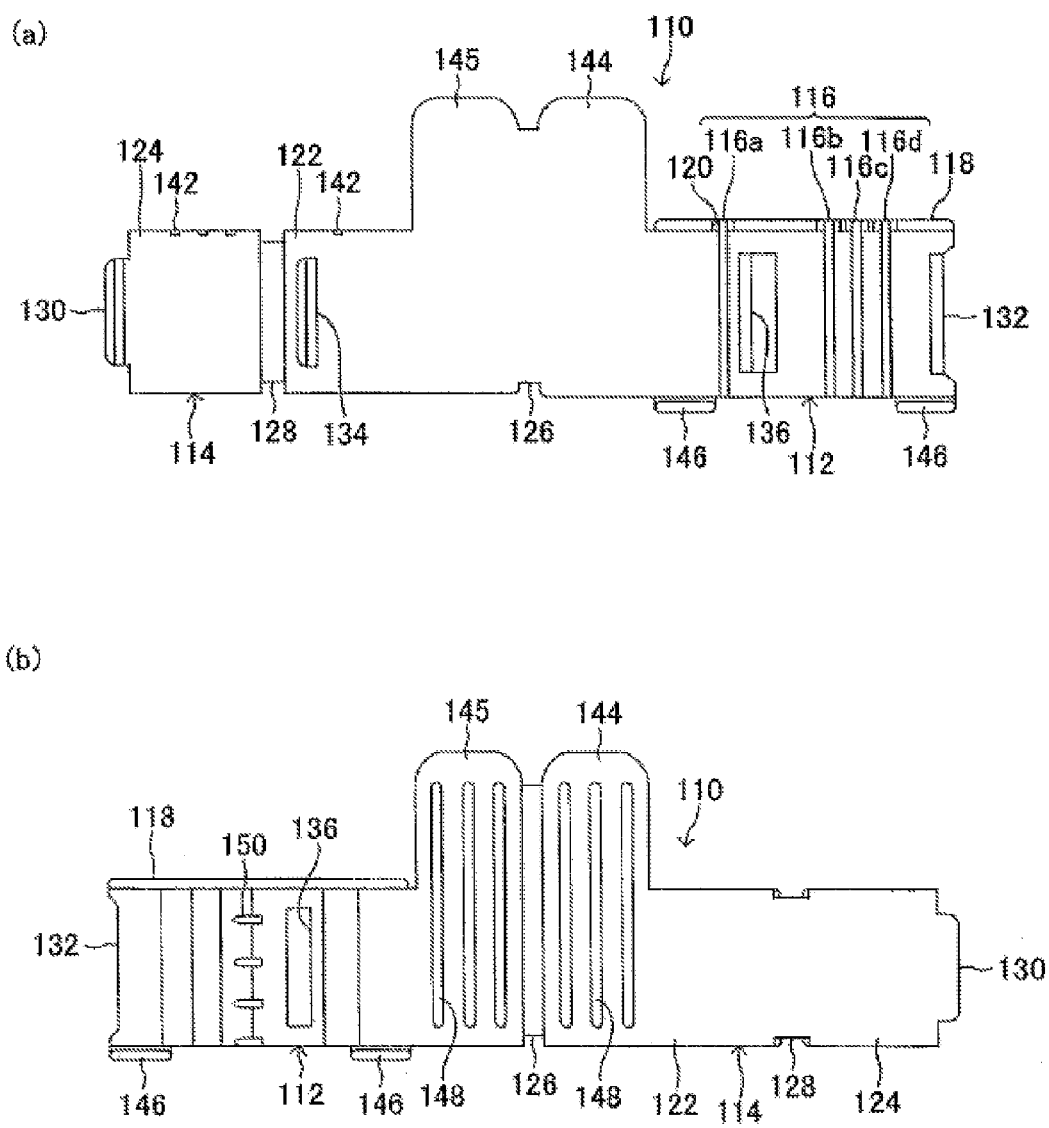
FIG. 3 is a front (a) and back (b) view of the puncturing needle assisting tool according to the first embodiment.
Figure 4:
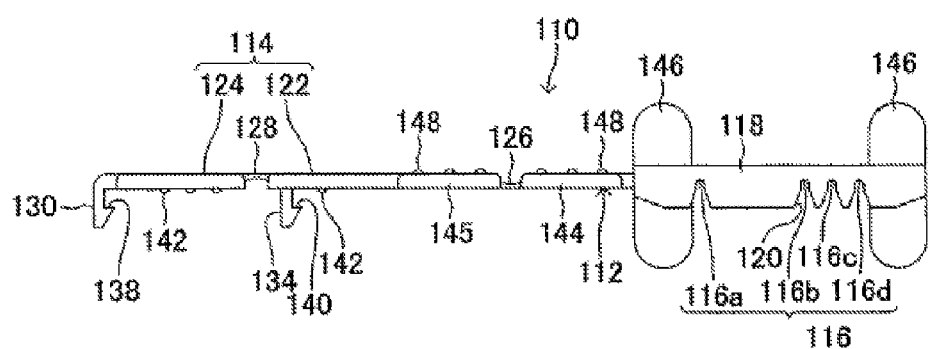
FIG. 4 is a top (a) and bottom (b) view of the puncturing needle assisting tool according to the first embodiment.
Figure 4:
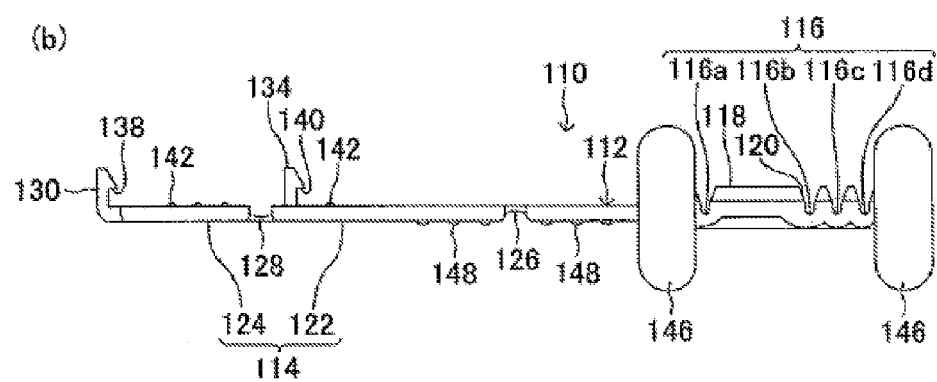
Figure 5:
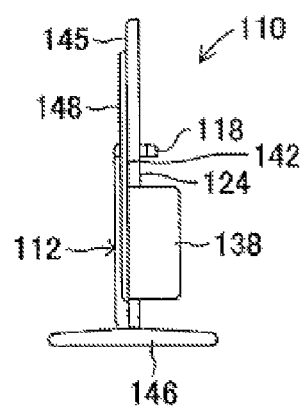
FIG. 5 is a left side (a) and right side (b) view of the puncturing needle assisting tool according to the first embodiment.
Figure 5:
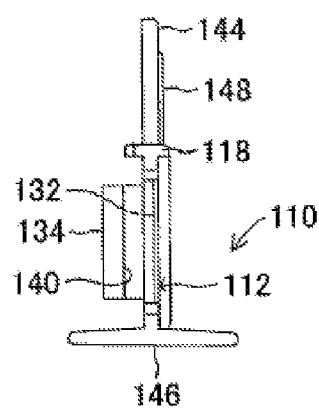
Figure 6:
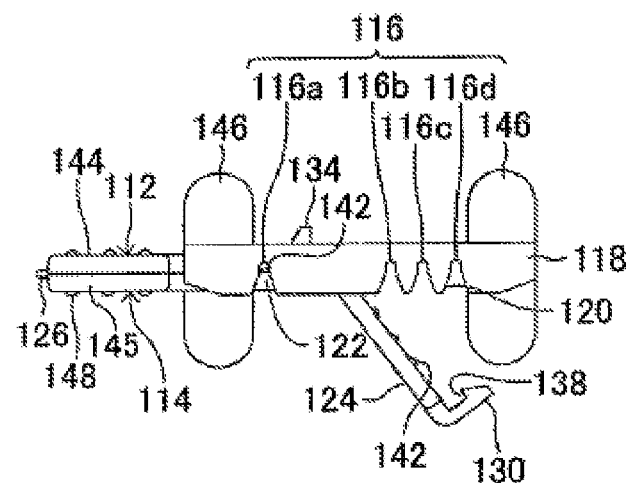
FIG. 6(a) is a top view of the puncturing needle assisting tool according to the first embodiment showing a first rotating portion in the closed position and a second rotating portion in the open position.
FIG. 6(b) is a top view of the puncturing needle assisting tool according to the first embodiment showing both the first rotating portion and the second rotating portion in the closed position.
Figure 6:
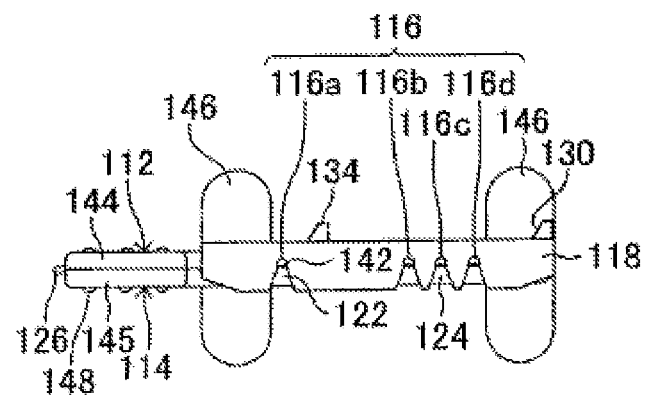
Figure 7:
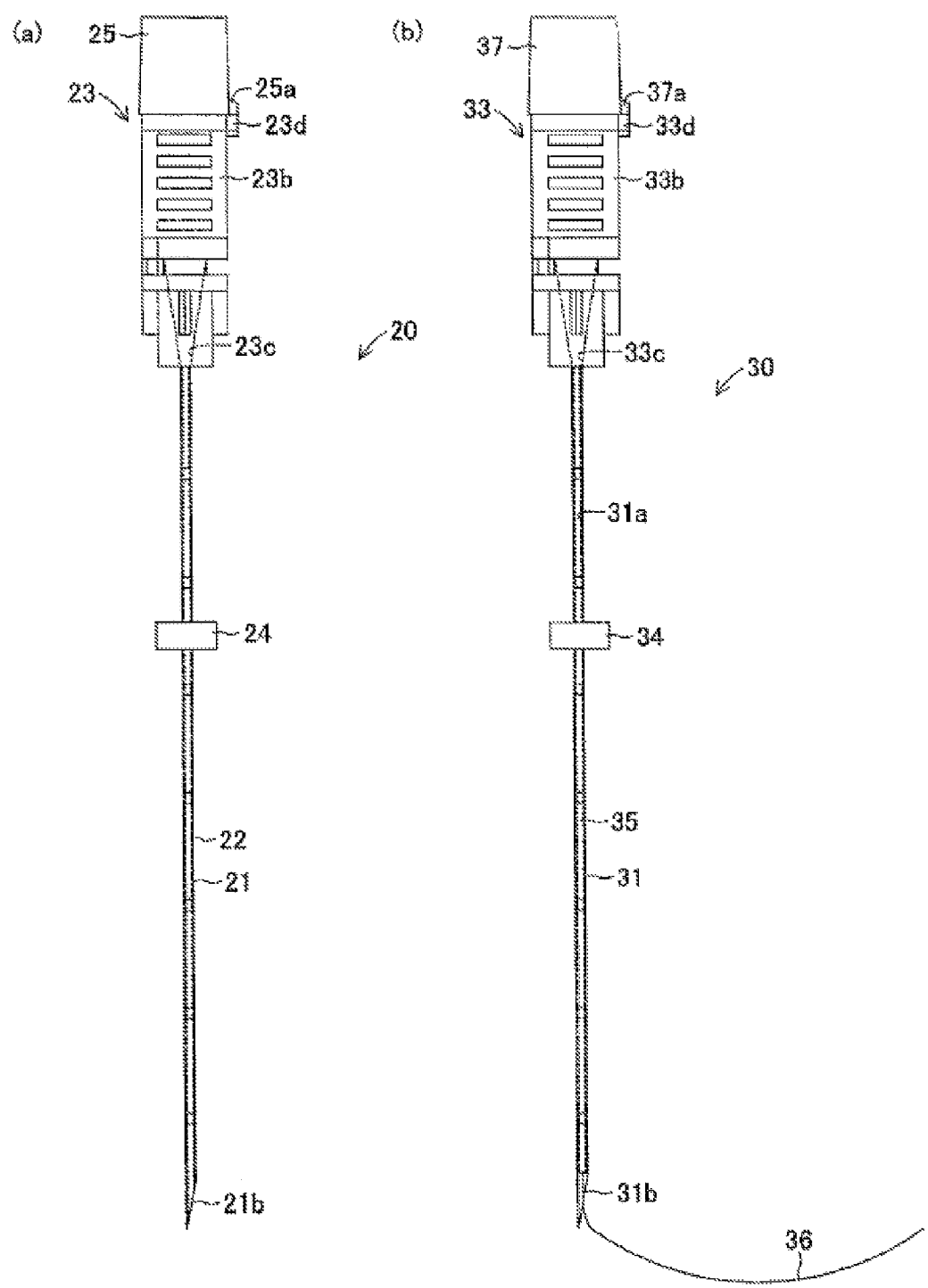
FIG. 7(a) is a top view of an insertion puncturing needle.
FIG. 7(b) is a top view of an extraction puncturing needle.

As shown in FIG. 1 to FIG. 3, the puncturing needle assisting tool 110 is provided with a planar assisting tool main unit 112, and a planar rotating member 114 that is attached rotatably to one edge portion of the assisting tool main unit 112. A plurality of guide grooves 116 are provided arrayed in parallel on the surface of the assisting tool main unit 112. Note that in the explanation below, the direction in which the guide grooves 116 extend (the groove direction) will be the vertical direction, and the direction in which the guide grooves 116 are arrayed will be the horizontal direction, based on the vertical direction and the horizontal direction in FIG. 3(a). The guide groove 116 is formed standing in the vertical-direction dimension of the assisting tool main unit 112, and has a semicircular shape in the horizontal cross section that is perpendicular to the groove direction. The back surface of the assisting tool main unit 112 corresponding to the groove bottom of the guide groove 116 protrudes in a semicircular shape, when viewed from the vertical direction (FIG. 2 and FIG. 4(b)). An outer insertion puncturing needle 21 (FIG. 8(a)) of an insertion puncturing needle 20 (FIG. 7(a)), and an extraction puncturing needle 30 (FIG. 7(b)), are placed in guide grooves 116 as puncturing needles, and are enabled to slide in the axial direction (the vertical direction) in the guide grooves 116. A protruding edge portion 118 is provided at the top end portion of the assisting tool main unit 112. The protruding edge portion 118 protrudes to both the surface side (the front side) and the back surface side of the assisting tool main unit 112. With the exception of the portion on the left side of the assisting tool main unit 112, the protruding edge portion 118 is provided at approximately ⅔ of the length dimension in the horizontal direction of the portion on the right side. Guide notches 120, formed on the top end side of the guide groove 116, are formed in the protruding edge portion 118. The guide notches 120 are wider towards the front side, so as to be guides for placing puncturing needles into the guide grooves 116.

The rotating member 114 comprises a first rotating portion 122 and a second rotating portion 124 on the left and the right respectively, along the direction in which the guide grooves 116 extend, and along a direction essentially perpendicular thereto. The first rotating portion 122 is attached to the assisting tool main unit 112 by connecting together, through a first hinge connecting portion 126 as the main unit attachment portion (also designated by the reference number 126), the edge portions that are essentially parallel to the direction in which the guide grooves 116 extend (i.e., the edge portion on the right side of the first rotating portion 122 and the edge portion on the left side of the assisting tool main unit 112—see FIG. 3(a)). The first hinge connecting portion 126 is thinner than the other portions as illustrated in FIG. 4(a) and FIG. 4(b). With the first hinge connecting portion 126 in the center, the first rotating portion 122 can be rotated (by bending at the first hinge connecting portion 126) from the open position wherein the surface openings of the guide grooves 116 are open towards the surface of the assisting tool main unit 112 the closed position (FIG. 6(a)), wherein the surface openings of the guide grooves 116 are closed. The second rotating portion 124 is attached to the first rotating portion 122 by connecting together, through a second hinge connecting portion 128, the edge portions that are essentially parallel to the direction in which the guide grooves 116 extend (i.e., the edge portion on the right side of the second rotating portion 124 and the edge portion on the left side of the first rotating portion 122—see FIG. 3(a)). The first hinge connecting portion 126 is thinner than the other portions. (FIG. 4(a) and FIG. 4(b)). With the second hinge connecting portion 128 in the center, the second rotating portion 124 can rotate relative to the first rotating portion 122 (by bending at the second hinge connecting portion 128). When the first rotating portion 122 is in the closed position, the second rotating portion 124 can rotate towards the surface of the assisting tool main unit 112 from the open position to the closed position (FIG. 6(b)). When either the first rotating portion 122 or the second rotating portion 124 is in the closed position (FIG. 6(b)), a rotating member 114 will lay on the front surface of the assisting tool main unit 112, where the top end surface of the rotating member 114 will follow the bottom surface of the protruding edge portion 118 of the assisting tool main unit 112. As a result, the bottom end surface of the rotating member 114 will be at the same height as the bottom end surface of the assisting tool main unit 112.

There are four guide grooves 116. There is one first guide groove 116a, and three seconds guide grooves 116b, 116c, and 116d. The first guide groove 116a is positioned in essentially the center part and in the horizontal direction of the assisting tool main unit 112, nearest the first hinge connecting portion 126. The second guide grooves 116b, 116c, and 116d, sequentially further to the right from the first hinge connecting portion 126, are positioned in the portion on the right side that is the opposite side of the first hinge connecting portion 126 from the assisting tool main unit 112. The spacing between the first guide groove 116a and the second guide groove 116b is wider, and the spacings between the second guide groove 116b, 116c, and 116d are either relatively narrower or the same. The surface opening of the first guide groove 116a is closed when the first rotating portion 122 is in the closed position. In this closed position, the first rotating portion 122 is in contact with the peripheral surface of the puncturing needle that is placed in the first guide groove 116a. Furthermore, the surface openings of the second guide grooves 116b, 116c, and 116d are closed when the second rotating portion 124 is in the closed position. In this closed position, the second rotating portion 124 is in contact with the peripheral surfaces of the puncturing needles that are placed in the second guide grooves 116b, 116c, and 116d.

The assisting tool main unit 112 and the rotating member 114 are provided with a lock so as to maintain the closed position of the rotating member 114. The lock is structured from a first rotating portion lock and a second rotating portion lock. The first rotating portion lock comprises a locking protrusion 134 and a locking hole 136, as the interlocking portion. The locking protrusion 134 forms a protrusion along the edge portion and on the side opposite from the first hinge connecting portion 126 of the first rotating portion 122, except for in the top and bottom portions; in this manner, the locking protrusion 134 is long in the vertical direction and stands on the front surface of the first rotating portion 122. The locking hole 136 is rectangular and is longer in the vertical direction of the assisting tool main unit 112 corresponding to the edge portion wherein the locking protrusion 134 of the first rotating portion 122 is provided; i.e., between the first guide groove 116a and the second guide groove 116b of the assisting tool main unit 112.

The second rotating portion lock comprises a locking protrusion 130 and a locking notch 132, as the interlocking portion. The locking protrusion 130 is formed along the edge portion on the side opposite from the first hinge connecting portion 126 of the rotating member 114 (i.e., the edge portion on the side opposite from the second hinge connecting portion 128 of the second rotating portion 124), except in the top and bottom portions, so as to be long vertically and so as to bend towards the front. The locking notch 132 is rectangular and is longer in the vertical direction in a portion of the assisting tool main unit 112 corresponding to the edge portion wherein the locking protrusion 130 of the second rotating portion 124 is provided; i.e., in the edge portion on the side opposite from the first hinge connecting portion 126 of the assisting tool main unit 112.

The locking protrusions 130 and 134 are both formed identically, wherein steps 138 and 140 are formed in the middle in the protruding direction, wherein the tip portions of the locking protrusions 130 and 134 are wedge-shaped. Inclined surfaces facing from the front surface side to the back surface side of the assisting tool main unit 112 are formed on the notched edge of the locking notch 132 and the hole edge of the locking hole 136. In accordance with the closing action of the first rotating portion 122, the inclined surface of the portion of the wedge-shaped of the locking protrusion 134 makes contact with the inclined surface of the portion of the hole edge of the locking hole 136, so that the locking protrusion 134 elastically interlocks removably with the locking hole 136 so that the step 140 of the locking protrusion 134 catches on the hole edge of the locking hole 136 to maintain the first rotating portion 122 in the closed position. Furthermore, in accordance with the closing action of the second rotating portion 124, the inclined surface of the portion of the wedge-shaped of the locking protrusion 130 makes contact with the inclined surface of the portion of the notch edge of the locking notch 132, so that the locking protrusion 130 elastically interlocks removably with the locking notch 132 so that the step 138 of the locking protrusion 130 catches on the hole edge of the locking notch 132 to maintain the second rotating portion 124 in the closed position.

Four resisting protrusions 142 are provided on the rotating member 114 (one on the first rotating portion 122 and three on the second rotating portion 124) so as to face the guide groove 116 in the closed position of the rotating member 114, that is, so as to face the first guide groove 116a in the closed position of the first rotating portion 122, and so as to face the second guide grooves 116b, 116c, and 116d in the closed position of the second rotating portion 124. The resisting protrusions 142 are semicircular plate shapes when viewed from the vertical direction, and are provided protruding at the positions of the heights of the top end portions of the rotating members 114 at positions that are in the centers of the semicircles of the guide grooves 116, which have a semicircular shape in their cross sections. The resisting protrusions 142 make point contacts with the peripheral surfaces of the puncturing needles that are placed in the guide grooves 116, to apply sliding resistance to the puncturing needles to prevent the puncturing needles from falling out under their own weight.

Grip portions 144 and 145 are formed, respectively, on the assisting tool main unit 112 and the first rotating portion 122. The grip portion 144 of the assisting tool main unit 112 and the grip portion 145 of the first rotating portion 122 lay together when the first rotating portion 122 is in the closed position, so as to be positioned facing between the first hinge connecting portion 126 and the guide groove 116 that is nearest to the first hinge connecting portion 126 (the first guide groove 116a). The top end portions of the grip portions 144 and 145 are higher than the positions of height of the left side of the protruding edge portion 118 so as to avoid the protruding edge portion 118, or in other words, extends about twice as high as the other portions of the assisting tool main unit 112 and the rotating member 114. As a whole, the assisting tool main unit 112 and the rotating member 114 are both dogleg shapes, and have linear symmetry around the first hinge connecting portion 126. Pinching the grip portions 144 and 145 enables the puncturing needle assisting tool 110 to be held, enabling the first rotating portion 122 to be rotated from the open position to the closed position.

A pair of stabilizing plates, both designated by 146, is formed integrally with the assisting tool main unit 112 at the bottom end of the assisting tool main unit 112. The stabilizing plates 146 are provided at the left side of the first guide groove 116a and at the right side of the second guide groove 116d, extending with the same length on both the front and back side of the assisting tool main unit 112 (FIG. 5(a) and FIG. 5(b)). Placing the bottom surface of the stabilizing plate 146 on the abdominal wall provides a sense of stability.

As a shown in FIG. 2 and FIG. 3(b), reinforcing ribs 148 are provided on the back surface of the grip portion 144 of the assisting tool main unit 112 and on the back surface of the grip portion 145 of the first rotating portion 122. The ribs 148, which extend in the vertical direction, are provided arrayed in the horizontal direction on the grip portions 144 and 145, except for in the top and bottom end portions of the grip portions 144 and 145. Reinforcing ribs 150 are also provided between the second guide groove 116b and the locking hole 136 on the back surface of the assisting tool main unit 112. The ribs 150 are arc shaped, extending horizontally when viewed from the vertical direction, and four ribs 150 are formed located with specific gaps in the vertical direction.

The outer insertion puncturing needle 21 of the insertion puncturing needle 20, and the extraction puncturing needle 30 will be explained prior to explaining the operation.

The insertion puncturing needle 20, as shown in FIG. 7(a) is provided with an outer insertion puncturing needle 21 and an inner insertion puncturing needle 22. The outer insertion puncturing needle 21, as shown in FIG. 8(a) is formed into a stainless steel tube, and the inside of the outer insertion puncturing needle 21 has a passage hole 21a through which the inner insertion puncturing needle 22 (FIG. 8(b)) passes. A resin hub portion 23 is attached at the base end portion (the top end portion) of the outer insertion puncturing needle 21. In the hub portion 23, the top portion 23a is formed as a small diameter round shape, and moving towards the bottom side from the center of the hub portion 23, the hub main unit 23b is formed into a square tube shape (having four side surfaces) that is wider than in the top portion 23a. A guide hole 23c, which connects to the passage hole 21a, is formed on the inside of the hub portion 23.

The guide hole 23c is formed so that the top portion side has a large diameter and the bottom portion side has a small diameter. This makes it easy to insert the inner insertion puncturing needle 22 into the inside of the passage hole 21a from above the hub portion 23. An annular interlocking portion 23d, wherein a hole portion is provided passing vertically therethrough, is provided on one side surface of the top end portion of the peripheral surface of the hub main unit 23b. The tip portion (the bottom end portion) of the outer insertion puncturing needle 21 is cut in the diagonal direction corresponding to the annular interlocking portion 23d. The orientation that is the sideways direction of the opening portion 21b and the orientation of the placement of the annular interlocking portion 23d are the same when viewed from the axial direction of the outer insertion puncturing needle 21. The sideways orientation of the opening portion 21b can be confirmed by the position of the annular interlocking portion 23d.

A planar positioning portion 24 is attached below the hub portion 23 of the outer insertion puncturing needle 21, with a gap from the hub portion 23. The outer insertion puncturing needle 21 is inserted into a hollow portion that is formed in the center portion of the positioning portion 24, enabling the attachment position of the positioning portion 24 to be varied relative to the outer insertion puncturing needle 21. The attachment position of the positioning portion 24 relative to the outer insertion puncturing needle 21 can be set as appropriate depending on the distance of protrusion that is required for the outer insertion puncturing needle 21 in the portion below the positioning portion 24 (which is the sum of the length of the insertion into the portion to be sutured and the distance between the top surface of the protruding edge portion 118 of the puncturing needle assisting tool 110 and the bottom surface of the stabilizing plate 146).

As a shown in FIG. 8(b), the inner insertion puncturing needle 22 is formed as a fine diameter rod member made from stainless steel that can pass through the inside of the passage hole 21a of the outer insertion puncturing needle 21. A resin hub portion 25 is attached at the base end portion (the top end portion) of the inner insertion puncturing needle 22. The hub portion 25 is formed as a square column shape (having four side surfaces). An indented portion (not shown), capable of accommodating the top portion 23a of the hub portion 23, is formed on the bottom portion side of the hub portion 25. A locking protrusion 25a that can be inserted into the hollow portion of the annular interlocking portion 23d is formed on one side surface of the bottom end portion of the peripheral surface of the hub portion 25. The bottom end portion of the locking protrusion 25a extends downward. The tip portion (the bottom end portion) of the inner insertion puncturing needle 22 is cut in the diagonal direction corresponding to the locking protrusion 25a. The orientation of the cut surface 22a that has been caught (a direction that is perpendicular to the axial direction) and the orientation of placement of the locking protrusion 25a are the same when viewed from the axial direction of the inner insertion puncturing needle 22. The orientation of the cut surface 22a can be confirmed by the position of the locking protrusion 25a.

Figure 8:
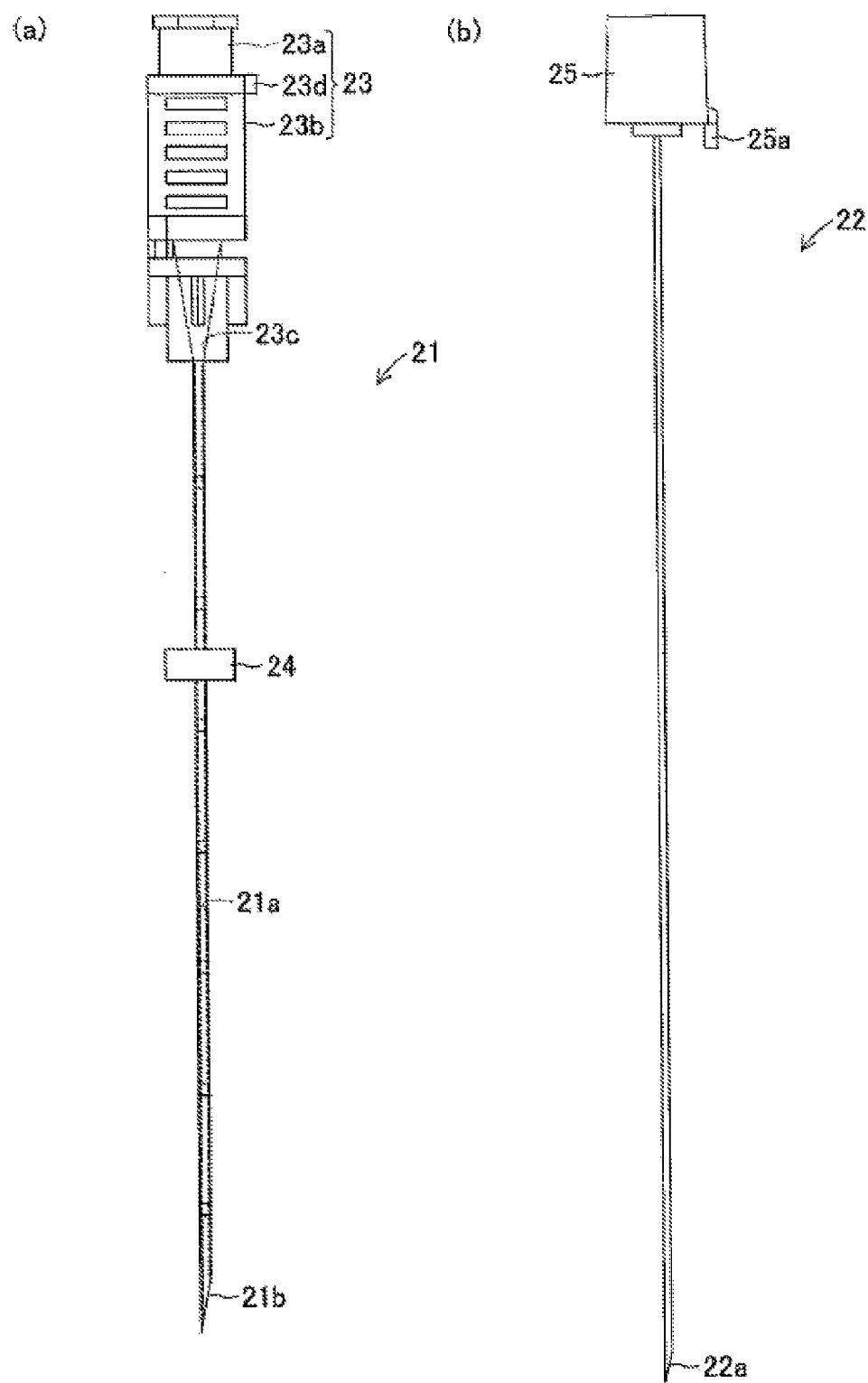
FIG. 8(a) is a top view of an outer insertion puncturing needle.
FIG. 8(b) is a top view of an inner insertion puncturing needle.

As is illustrated in FIG. 7(a) and FIG. 8, when the inner insertion puncturing needle 22 is inserted into the passage hole 21a of the outer insertion puncturing needle 21, the top portion 23a of the hub portion 23 of the outer insertion puncturing needle 21 enters into the inner portion of the hub portion 25 of the inner insertion puncturing needle 22, and the locking protrusion 25a of the hub portion 25 of the inner insertion puncturing needle 22 interlocks with the annular interlocking portion 23d of the hub portion 23 of the outer insertion puncturing needle 21 so that the cut surface 22a of the inner insertion puncturing needle 22 will be oriented the same as the opening portion 21b of the outer insertion puncturing needle 21 within the passage hole 21a of the outer insertion puncturing needle 21. When not in use, a tubular protector 26 is attached to the insertion puncturing needle 20 with the inner insertion puncturing needle 22 assembled into the outer insertion puncturing needle 21, as shown in FIG. 10(a). With the puncturing needle portion of the insertion puncturing needle 20 housed within the protector 26, the bottom end portion of the hub portion 23 of the outer insertion puncturing needle 21 interlocks with the inner peripheral portion of the opening of the protector 26 so as to protect the puncturing needle portion of the insertion puncturing needle 20.

Figure 9:
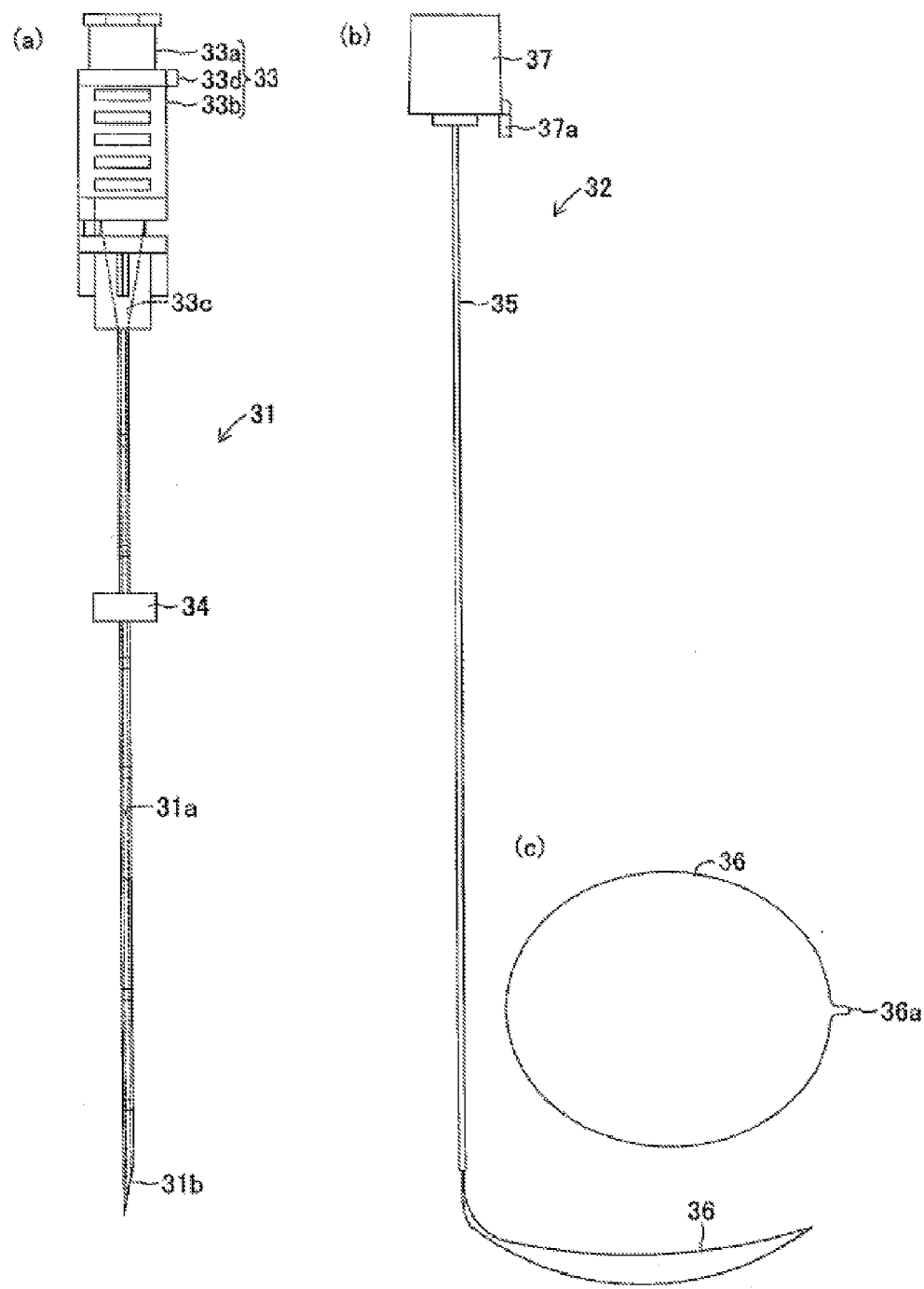
FIG. 9(a) is a top view of an outer extraction puncturing needle.
FIG. 9(b) is a top view of an inner extraction puncturing needle.
FIG. 9(c) is a top view of a snare portion of the inner extraction puncturing needle.
Figure 10:
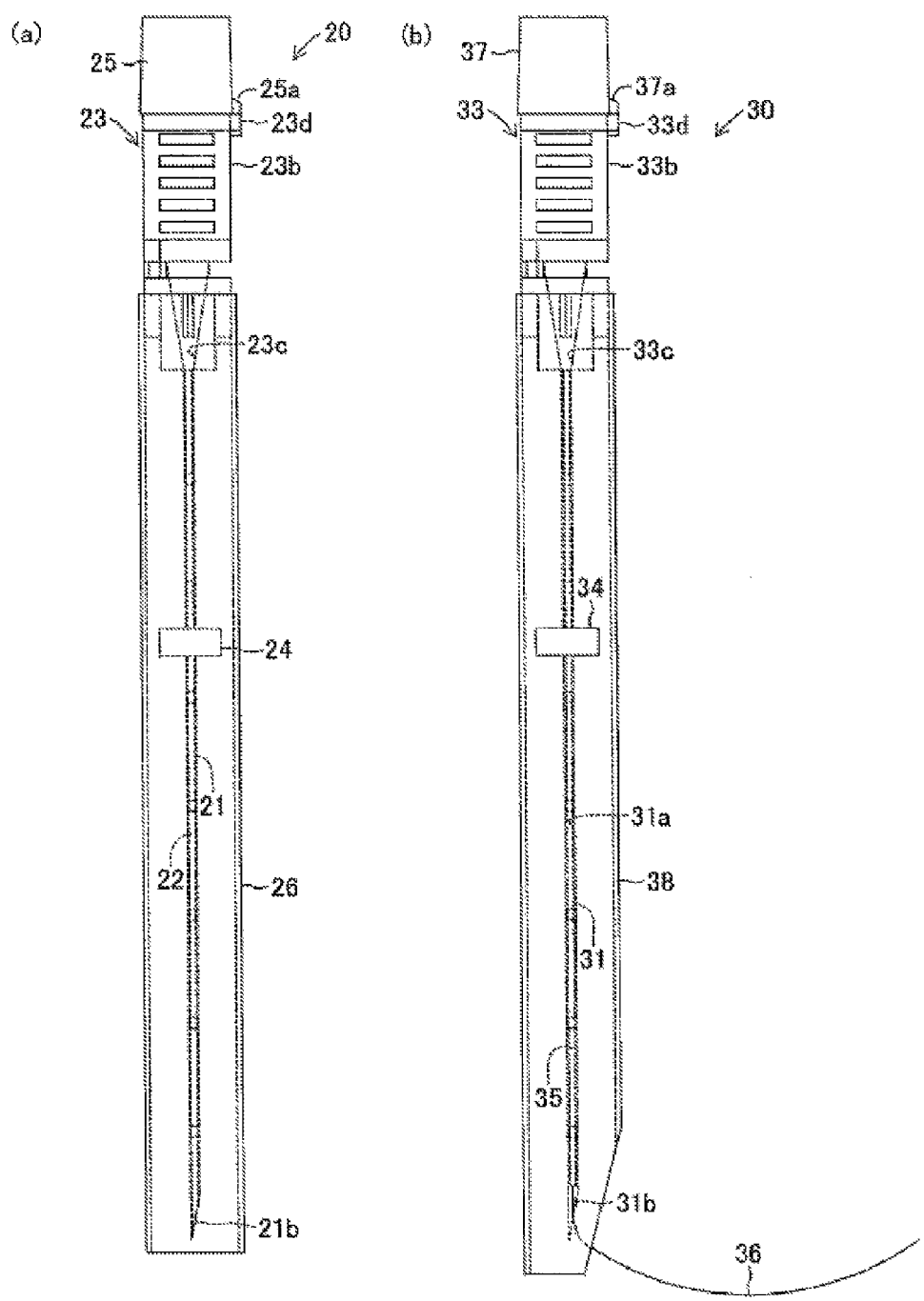
FIG. 10(a) is a top view showing a protector attached to the insertion puncturing needle.
FIG. 10(b) is a top view showing the protector attached to the extraction puncturing needle.

The extraction puncturing needle 30, as shown in FIG. 7(b) and FIG. 9, is provided with an outer extraction puncturing needle 31 and an inner extraction puncturing needle 32. As shown in FIG. 9(a), the outer extraction puncturing needle 31 is formed into a stainless steel tube, and a passage hole 31a, through which the inner extraction puncturing needle 32 passes, is formed in the inside thereof. A resin hub portion 33 is attached at the base end portion (the top end portion) of the extraction puncturing needle outer needle 31. In the hub portion 33, the top portion 33a is formed as a small diameter round shape, and moving towards the bottom side from the center of the hub portion 33, the hub main unit 33b is formed into a square tube shape (having four side surfaces) that is wider than in the top portion 33a. A guide hole 33c, which connects to the passage hole 31a, is formed on the inside of the hub portion 33.

The guide hole 33c is formed so that the top portion side has a large diameter and the bottom portion side has a small diameter. This makes it easy to insert the inner extraction puncturing needle 32 into the inside of the passage hole 31a from above the hub portion 33. An annular interlocking portion 33d, wherein a hole portion is provided passing vertically therethrough, is provided on one side surface of the top end portion of the peripheral surface of the hub main unit 33b. The tip portion (the bottom end portion) of the outer extraction puncturing needle 31 is cut in the diagonal direction corresponding to the annular interlocking portion 33d. An opening portion 31b is formed by cutting so as to be open in a sideways direction (perpendicular to the axial direction of the outer extraction puncturing needle 31). The orientation that is the sideways direction of the opening portion 31b and the orientation of the placement of the annular interlocking portion 33d are the same when viewed from the axial direction of the outer extraction puncturing needle 31. The sideways orientation of the opening portion 31b can be confirmed by the position of the annular interlocking portion 33b.

A planar positioning portion 34 is attached below the hub portion 33 of the outer extraction puncturing needle 31, with a gap from the hub portion 33. The outer extraction puncturing needle 31 is inserted into a hollow portion that is formed in the center portion of the positioning portion 34, enabling the attachment position of the positioning portion 34 to be varied relative to the outer extraction puncturing needle 31. The attachment position of the positioning portion 34 relative to the outer extraction puncturing needle 31 can be set as appropriate depending on the distance of protrusion for the outer extraction puncturing needle 31 in the portion below the positioning portion 34 (which is the sum of the length of the insertion into the portion to be sutured and the distance between the top surface of the protruding edge portion 118 of the puncturing needle assisting tool 110 and the bottom surface of the stabilizing plate 146).

The inner extraction puncturing needle 32, as shown in FIG. 9(b), is provided with a fine diameter stainless steel inner needle portion 35 capable of passing through the inside of the passage hole 31a of the outer extraction puncturing needle 31, a looped snare portion 36 provided on the tip portion of the inner needle portion 35, and a hub portion 37 provided on the top end portion of the inner needle portion 35. A snare portion 36 is formed from an extremely fine line-shaped member, finer than the inner needle portion 35, and is bent to extend in essentially the horizontal direction from the tip portion of the inner needle portion 35. The shape of the snare portion 36 when viewed flat is essentially a circular shape (FIG. 9(c)), and the shape when viewed from the side is an arc shaped, arced with the center towards the bottom. A small U-shaped locking curve portion 36a is formed at the tip end portion of the snare portion 36 (FIG. 9(c)).

The snare portion 36 is flexible, and although the locking curve portion 36a deforms easily through the application of a slight force so as to separate from the tip portion of the inner needle portion 35 so as to extend straight, it returns to the original loop shape when the force causing the deformation is released. An indented portion (not shown), capable of accommodating the top portion 33a of the hub portion 33 of the outer extraction puncturing needle 31, is formed on the bottom portion side of the hub portion 37. A locking protrusion 37a is formed on the bottom end portion of one side surface of the four side surfaces of the hub portion 37 corresponding to the direction in which the snare portion 36 extends. The bottom end portion of the locking protrusion 37a extends in the downward direction, and can be inserted into the inside of the hollow portion of the annular interlocking portion 33d of the hub portion 33 of the outer extraction puncturing needle 31.

As is illustrated in FIG. 7(b) and FIG. 9, when the inner extraction puncturing needle 32 is inserted into the passage hole 31a of the outer extraction puncturing needle 31 in a state wherein the snare portion 36 of the inner extraction puncturing needle 32 extends in the form of a straight line, the top portion 33a of the hub portion 33 of the outer extraction puncturing needle 31 enters into the inner portion of the hub portion 37 of the inner extraction puncturing needle 32, and the locking protrusion 37a of the hub portion 37 of the inner extraction puncturing needle 32 interlocks with the annular interlocking portion 33d of the hub portion 33 of the outer extraction puncturing needle 31 so that the snare portion 36 of the inner extraction puncturing needle 32 will return to the loop shape, protruding to the outside from the opening portion 31b of the outer extraction puncturing needle 31.

When not in use, and essentially tubular protector 38 is attached to the extraction puncturing needle 30 with the inner extraction puncturing needle 32 assembled into the outer extraction puncturing needle 31, as shown in FIG. 0(b). The tip end portion of the protector 38 has a portion on one side that is cut at an angle, and includes a portion that is cut so as to be open. With the puncturing needle portion of the extraction puncturing needle 30 housed within the protector 38, when the bottom end portion of the hub portion 33 of the outer extraction puncturing needle 31 interlocks with the inner peripheral portion of the opening of the upper end portion of the protector 38 the puncturing needle portion of the extraction puncturing needle 30 is protected. The snare portion 36 of the inner extraction puncturing needle 32 protrudes from the opening in the tip end portion of the protector 38 so that there will be no external force on the snare portion 36. The shape of the snare portion 36 is maintained over an extended period of time.

In regards to the action of the first embodiment, an explanation will be given regarding a case wherein the puncturing needle assisting tool 110 is used to suture together the abdominal wall A and the gastric wall B.

Figure 11:
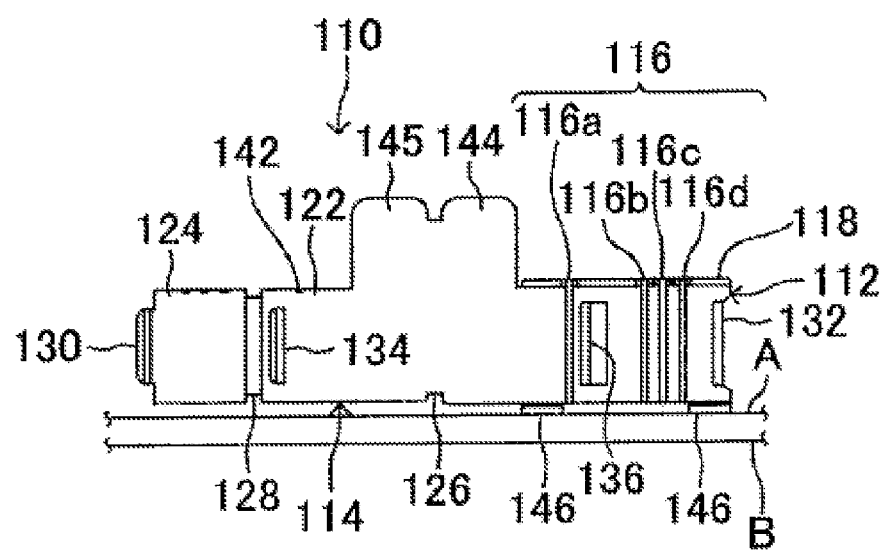
FIG. 11 is a top view of the puncturing needle assisting tool according to the first embodiment placed on the surface of the skin of the abdomen.
Figure 12:
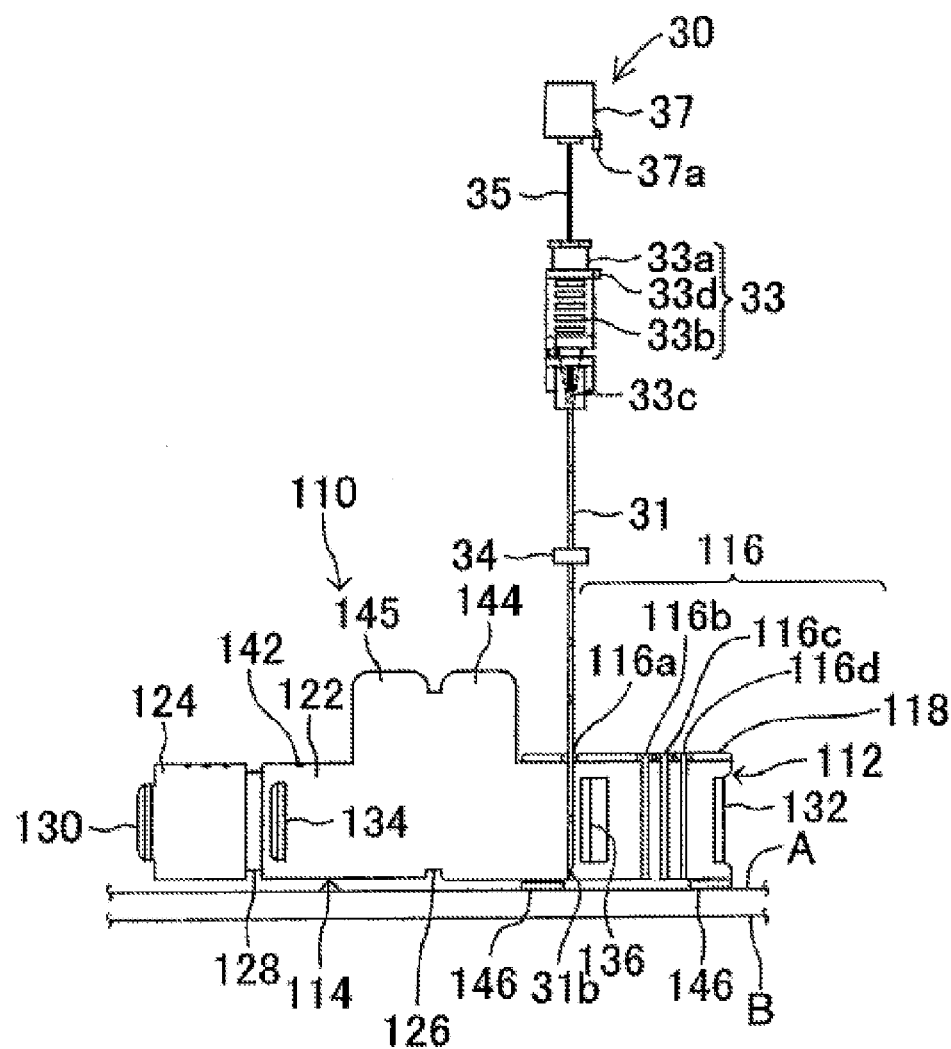
FIG. 12 is a top view of the puncturing needle assisting tool according to the first embodiment wherein the extraction puncturing needle is placed in a guide groove.

First, as shown in FIG. 11, the assisting tool main unit 112 is placed on the surface of the skin of the abdominal wall A of the patient. The grip portions 144 and 145 are grasped and the rotating member 114 is supported set, as shown in FIG. 12, the snare portion 36 of the inner extraction puncturing needle 32 will be housed within the outer extraction puncturing needle 31, and with the hub portion 37 of the inner extraction puncturing needle 32 positioned over the hub portion 33 of the outer extraction puncturing needle 31, the tip side portion of the extraction puncturing needle 30 enters into, and is positioned in, the first guide groove 116a within the guide grooves 116 of the assisting tool main unit 112. At this time, both the first rotating portion 122 and the second rotating portion 124 are in the open position.

Figure 13:
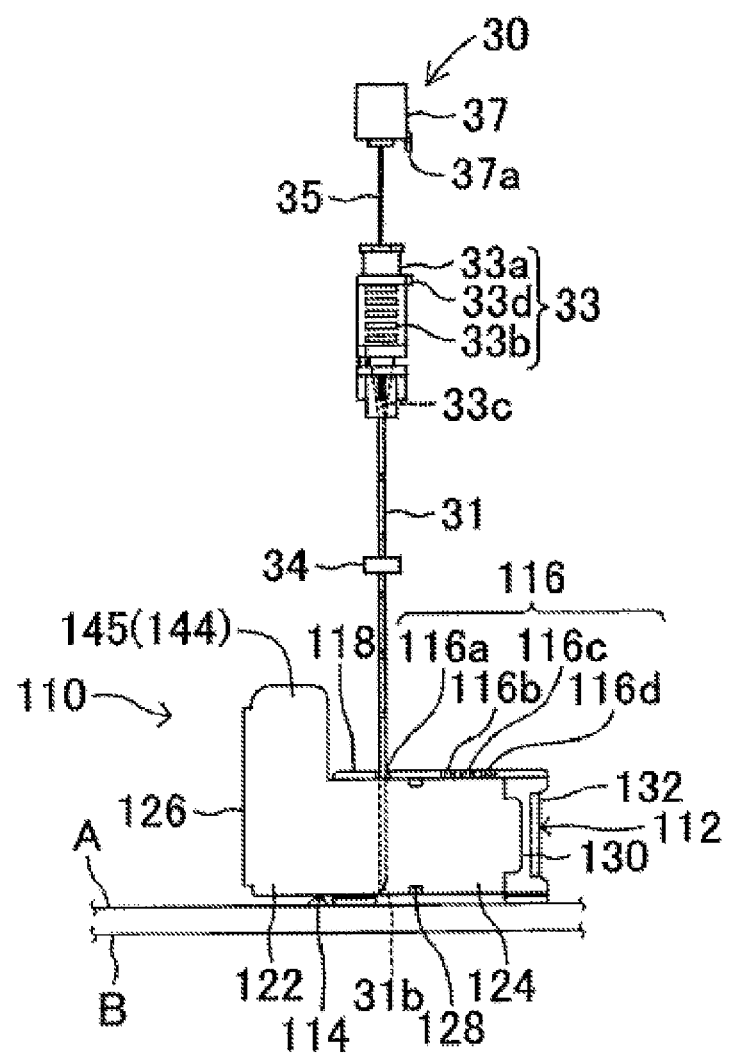
FIG. 13 is a top view of the puncturing needle assisting tool according to the first embodiment wherein the extraction puncturing needle is placed in the guide groove and the first rotating portion is rotated to a surface side of the assisting tool main unit.
Figure 14:
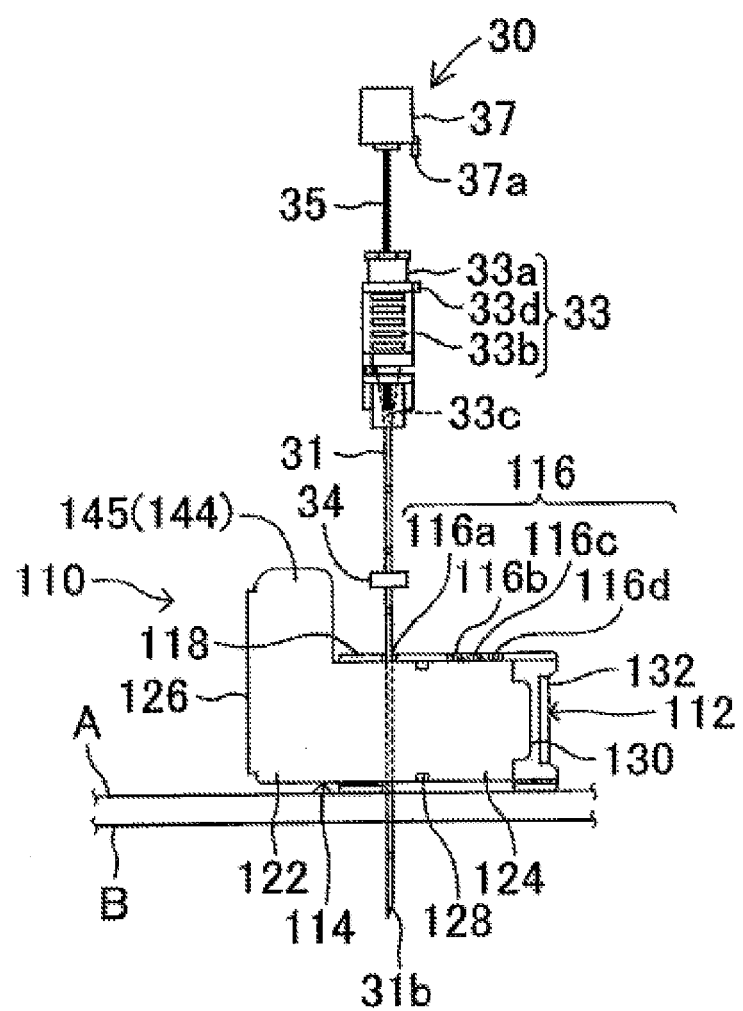
FIG. 14 is a top view of the puncturing needle assisting tool according to the first embodiment wherein the extraction puncturing needle has pierced the abdomen.

Next, if the grip portions 144 and 145 are grasped, then, as shown in FIG. 13, the first rotating portion 122 will rotate to the surface side of the assisting tool main unit 112 to the closed position from the open position, so that the first rotating portion 122 will lay on the surface of the assisting tool main unit 112. The locking protrusion 134 interlocks with the locking hole 136 to maintain the closed position of the first rotating portion 122, while, on the other hand, the second rotating portion 124 is in the open position. (See FIG. 6(a).) In the state, the extraction puncturing needle 30 is pressed against the surface of the skin on the abdominal wall A and, as illustrated in FIG. 14, moves down so that the first guide groove 116*a* and the first rotating portion 122 make contact, so that the tip end portion of the extraction puncturing needle 30 moves along the first guide groove 116*a* to puncture the abdominal wall A and the gastric wall B. Note that in FIG. 13 through FIG. 20 the puncturing needle assisting tool 110 is illustrated without the ribs 148.

Figure 15:
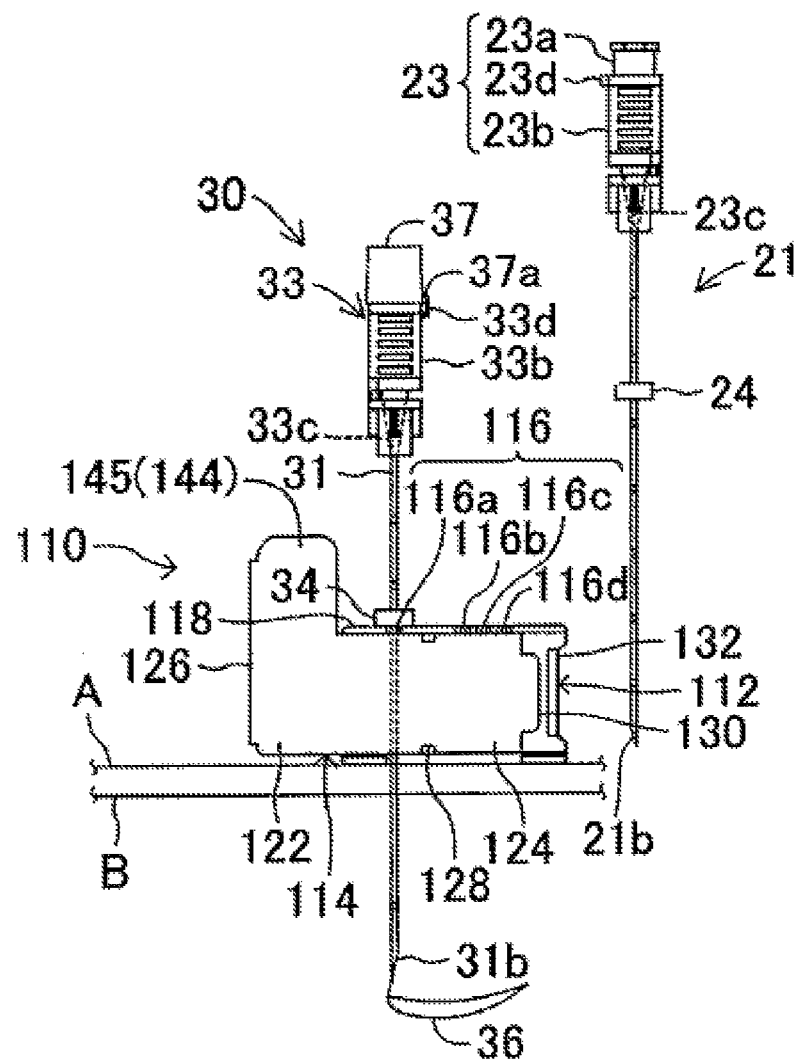
FIG. 15 is a top view of the puncturing needle assisting tool according to the first embodiment wherein the snare portion of the inner extraction puncturing needle is spread in the shape of a loop within the stomach.

Next, as illustrated in FIG. 15, the extraction puncturing needle 30 penetrates until the positioning portion 34 of the outer extraction puncturing needle 31 makes contact with the protruding edge portion 118 of the assisting tool main unit 112. Following this, when the inner extraction puncturing needle 32 moves within the outer extraction puncturing needle 31 and the locking protrusion 37*a* of the inner extraction puncturing needle 32 interlocks with the annular interlocking portion 33*d* of the outer extraction puncturing needle 31, the snare portion 36 of the inner extraction puncturing needle 32 will extend from the opening portion 31*b* of the outer extraction puncturing needle 31. The snare portion 36 of the inner extraction puncturing needle 32 will spread into a loop shape so as to be essentially perpendicular relative to the outer extraction puncturing needle 31 on the inside of the gastric wall B. The direction in which the snare portion 36 of the inner extraction puncturing needle 32 will expand can be confirmed by the positions of the locking protrusion 37*a* of the inner extraction puncturing needle 32 and the annular interlocking portion 33*d* of the outer extraction puncturing needle 31.

Figure 16:
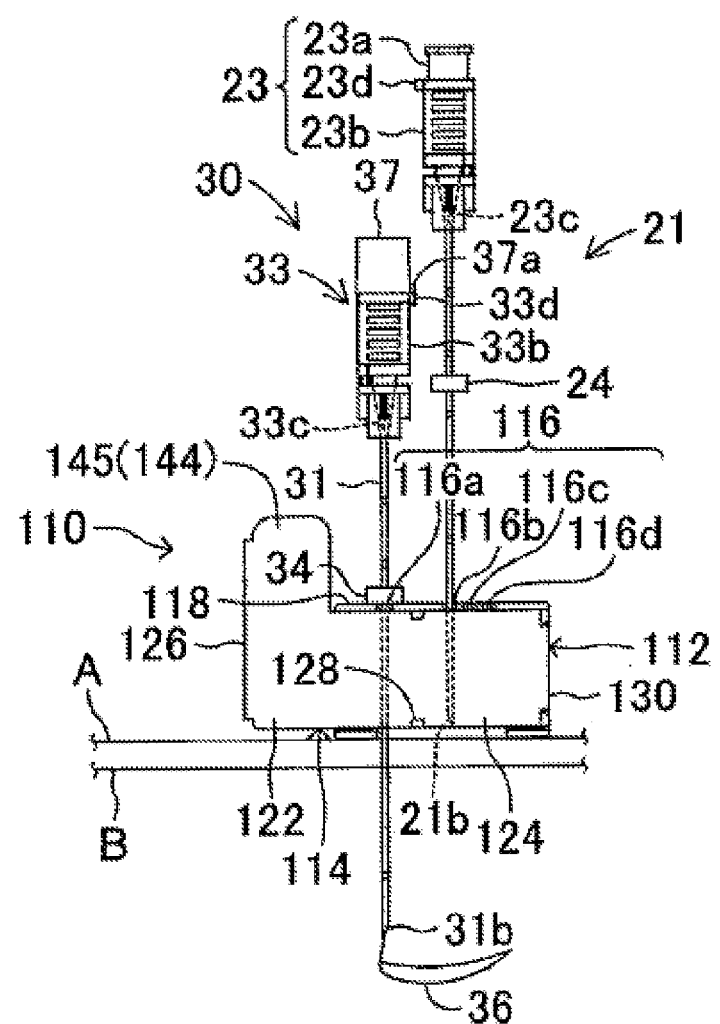
FIG. 16 is a top view of the puncturing needle assisting tool according to the first embodiment wherein an outer insertion puncturing needle is placed in the guide groove and the second rotating portion is rotated to the surface side of the assisting tool main unit.

Next, the inner insertion puncturing needle 22 is withdrawn from the outer insertion puncturing needle 21, and the tip end side portion of the outer insertion puncturing needle 21 enters into a second guide groove 116*b*, 116*c*, or 116*d* of the assisting tool main unit 112, for example, into the second guide groove 116*b* that is nearest to the first guide groove 116*a*, to be positioned therein. Next, if the assisting tool main unit 112 and the rotating portion 124 are pinched together, then, as shown in FIG. 16, the second rotating portion 124 will rotate to the surface side of the assisting tool main unit 112 to the closed position from the open position, so that the second rotating portion 124 will lay on the surface of the assisting tool main unit 112. (See FIG. 6(*b*).) The locking protrusion 130 interlocks with the locking notch 132 to maintain the closed position of the second rotating portion 124.

Figure 17:
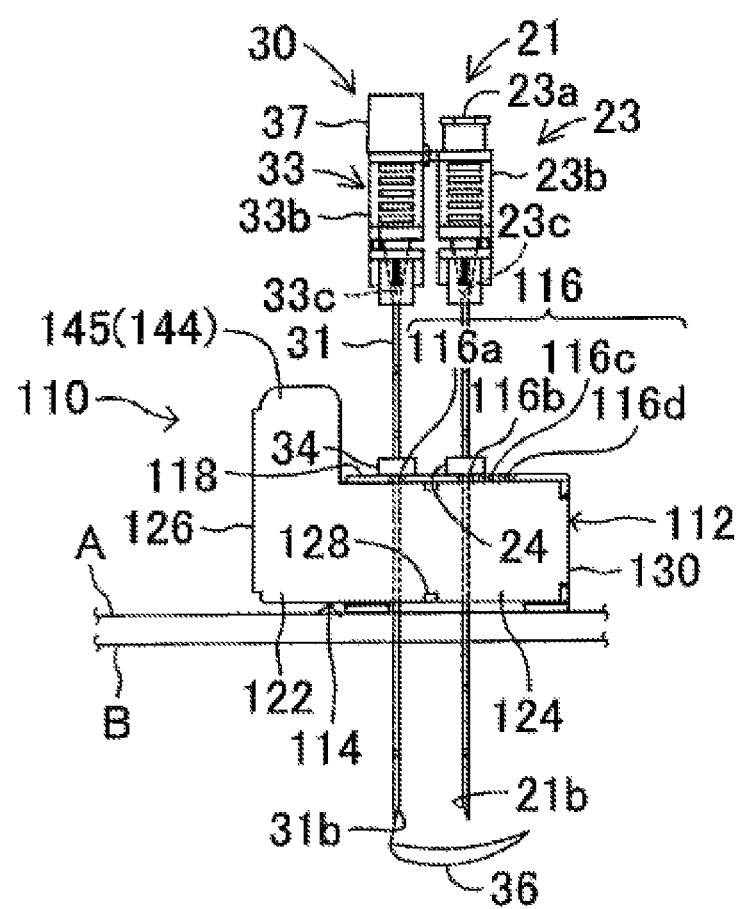
FIG. 17 is a top view of the puncturing needle assisting tool according to the first embodiment wherein the outer insertion puncturing needle has pierced the abdomen.

In this state, the outer insertion puncturing needle 21 is pressed against the surface of the skin on the abdominal wall A, and, as shown in FIG. 17, the outer insertion puncturing needle 21 moves along the second guide groove 116*b* until the positioning portion 24 of the outer insertion puncturing needle 21 makes contact with the protruding edge portion 118 of the assisting tool main unit 112, so that the tip end side portion of the outer insertion puncturing needle 21 will penetrate the abdominal wall A and the gastric wall B. The tip end portion of the outer insertion puncturing needle 21 will be positioned in the vicinity of the center of the snare portion 36 of the inner extraction puncturing needle 32. The annular interlocking portion 23*d* of the hub portion 23 of the outer insertion puncturing needle 21 facing the locking protrusion 37*a* of the hub portion 37 of the inner extraction puncturing needle 32 and facing the annular interlocking portion 33*d* of the hub portion 33 of the outer extraction puncturing needle 31 makes it possible for the opening portion 21*b* of the outer insertion puncturing needle 21 to face the opening portion 31*b* of the outer extraction puncturing needle 31.

Figure 18:
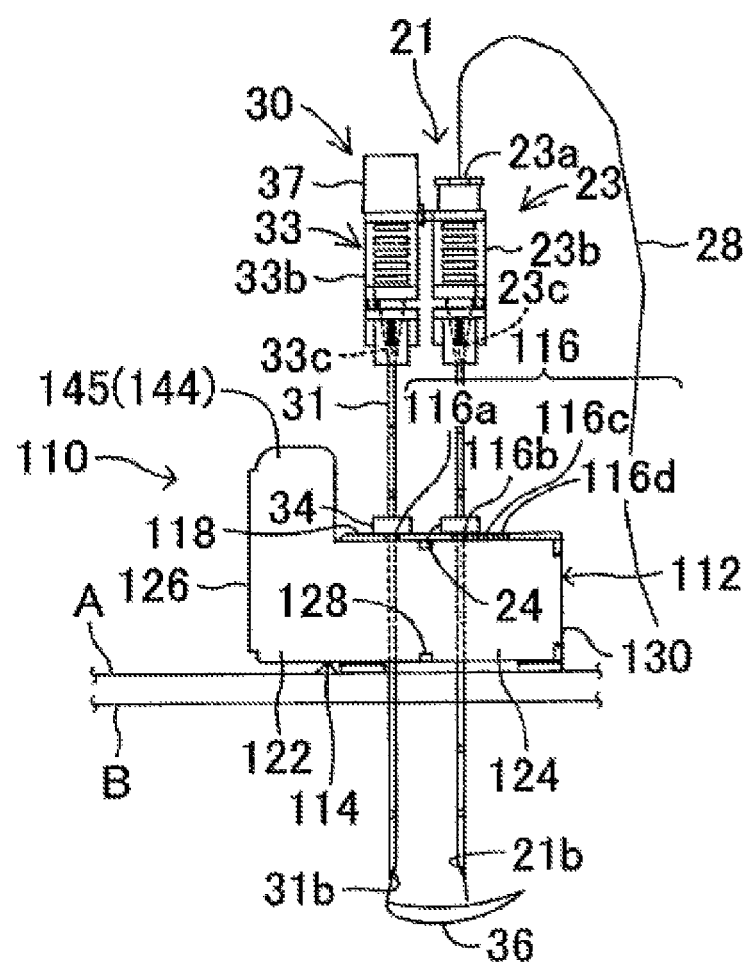
FIG. 18 is a top view of the puncturing needle assisting tool according to the first embodiment wherein a suture thread is inserted into the outer insertion puncturing needle.
Figure 19:
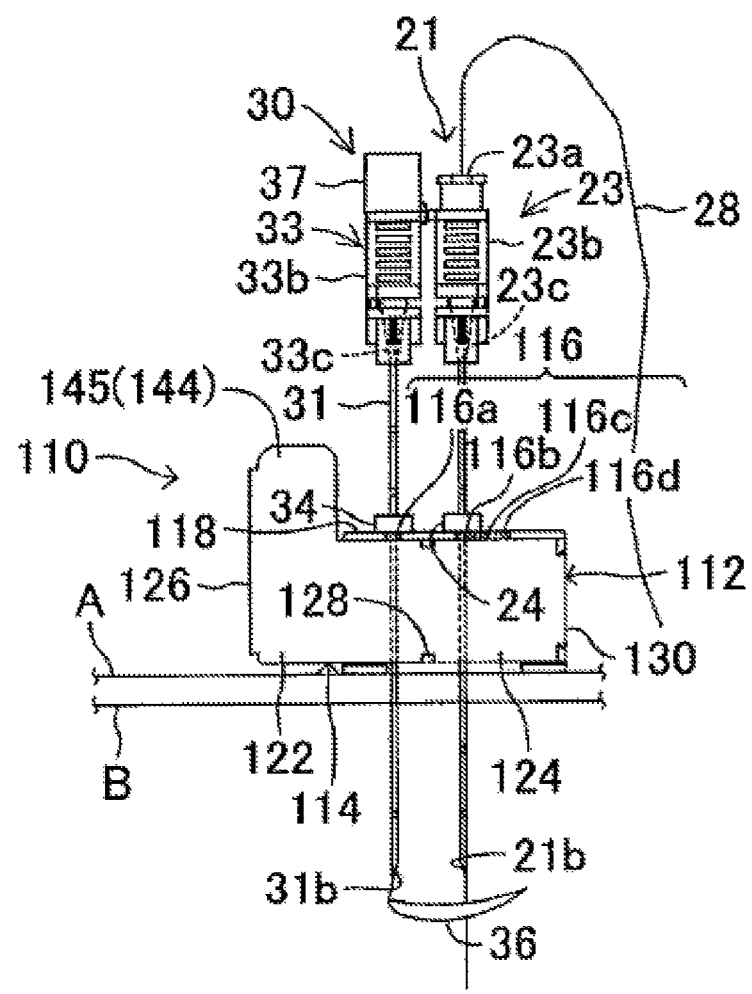
FIG. 19 is a top view of the puncturing needle assisting tool according to the first embodiment wherein the tip portion of the suture thread has passed through the inside of the snare portion of the inner extraction puncturing needle.
Figure 20:
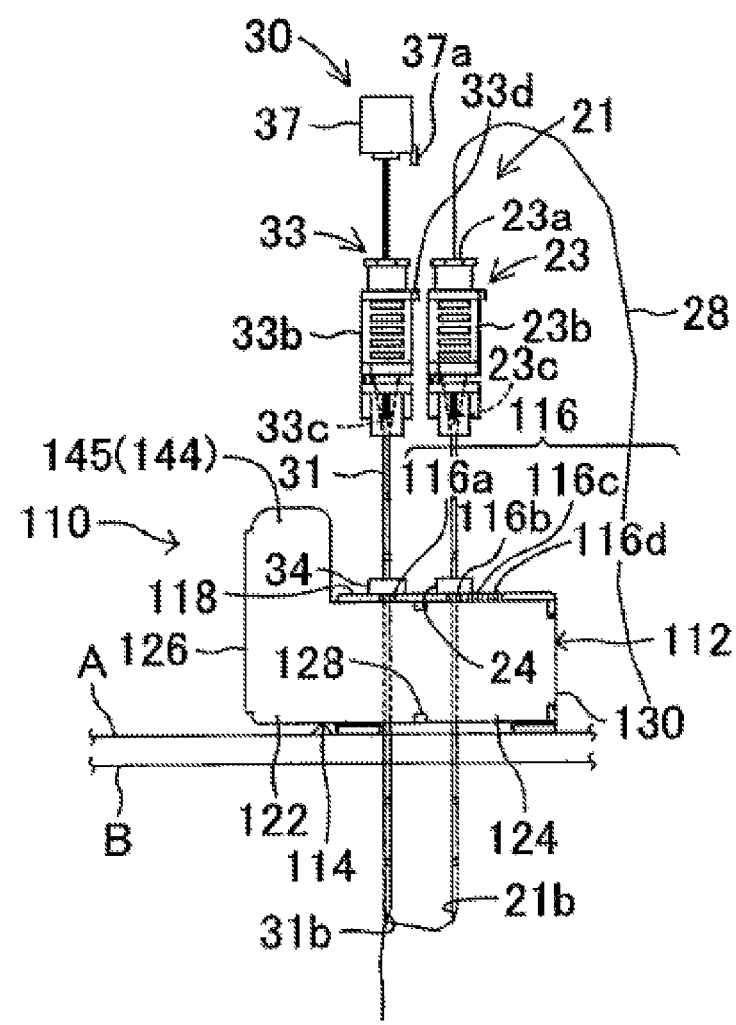
FIG. 20 is a top view of the puncturing needle assisting tool according to the first embodiment wherein the tip portion of the suture thread is inside the snare portion of the inner extraction puncturing needle and is inside the outer extraction puncturing needle.

Next, as illustrated in FIG. 18, the suture thread 28 is inserted into the passage hole 21*b* of the outer insertion puncturing needle 21 from the guide wall of the hub portion 23 of the outer insertion puncturing needle 21, and, as shown in FIG. 19, the tip end portion of the suture thread 28 will protrude from the opening portion 21*a* of the outer insertion puncturing needle 21. The tip end portion of the suture thread 28 and the snare portion 36 of the inner extraction puncturing needle 32 can be verified using an endoscope. If the tip end portion of the suture thread 28 is positioned within the snare portion 36, then, as illustrated in FIG. 20, the hub portion 37 of the inner extraction puncturing needle 32 is pulled upward so that the inner extraction puncturing needle 32 will move upward to the upper portion side of the outer extraction puncturing needle 31. The tip end portion of the suture thread 28 interlocks with the locking curve portion 36*a* of the snare portion 36 of the inner extraction puncturing needle 32, to enter into the inside of the outer extraction puncturing needle 31 along with the snare portion 36.

Figure 21:
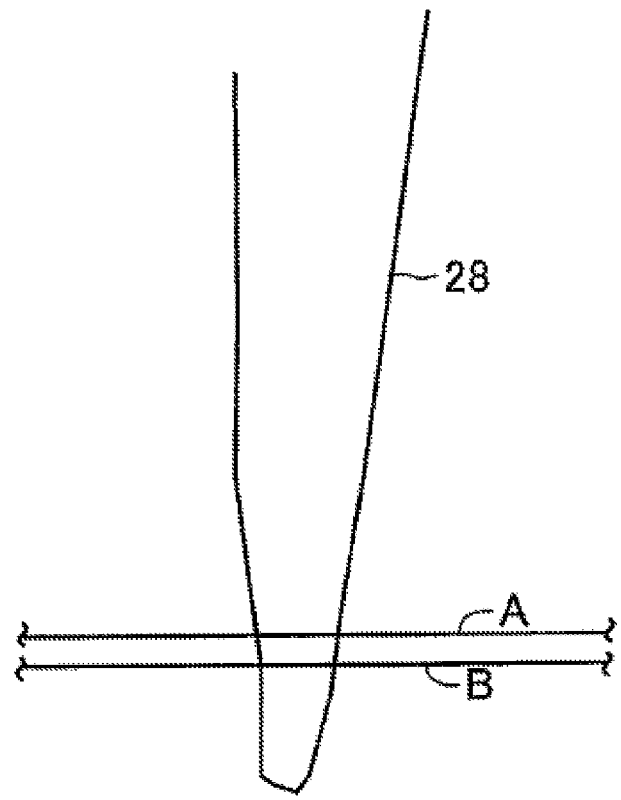
FIG. 21 is a top view showing that both ends of the suture threads have been extracted from the abdominal wall after removing the extraction needle assisting tool.
Figure 22:
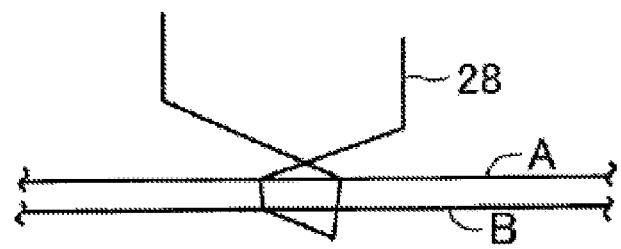
FIG. 22 is a top view showing the ends of the suture threads protruding from the abdominal wall after having been tied together.

Next, the outer insertion puncturing needle 21 and the extraction puncturing needle 30 are withdrawn from the body of the patient. Note that the puncturing needle assisting tool 110 is removed from the portion to be sutured, with the outer insertion puncturing needle 21 and the extraction puncturing needle 30 still positioned in the guide grooves 116. Both ends of the suture thread 28 pass through the gastric wall B and the abdominal wall A to extend on the outside of the patient, as illustrated in FIG. 21. When, as illustrated in FIG. 22, the end portions of the suture thread 28 are tied together, the suturing procedure has been completed.

Note that when inserting the suture thread 28 into the passage hole 21*a* of the outer insertion puncturing needle 21, the following should be performed when the suture thread 28 has become jammed within the passage hole 21*a*. If first the suture thread 28 is pulled back from the outer insertion puncturing needle 21 and the inner insertion puncturing needle 22 is inserted into the passage hole 21*a* to remove that which is jammed within the passage hole 21*a*, then, thereafter, the suture thread 28 can again the inserted into the passage hole 21*a* so that the tip end portion of the suture thread 28 will protrude from the opening portion 21*b*.

As described above, the assisting tool main unit 112 is placed on the surface of the skin of the abdominal wall of the patient, and with the first rotating portion 122 in the open state, the extraction puncturing needle 30 is positioned within a guide groove 116. In a state wherein the first rotating portion 122 is rotated on the outer surface of the assisting tool main unit 112 to the closed position, if the extraction puncturing needle 30 is pressed into the body, then the extraction puncturing needle 30 will move along the guide groove 116 and the tip side portion of the extraction puncturing needle 30 will puncture into the body. The same is also true for the second rotating portion 124, where the insertion puncturing needle 20 is positioned within the guide groove 116 while the second rotating portion 124 is in the open position. In a state wherein the second rotating portion 124 is rotated on the outer surface of the assisting tool main unit 112 to the closed position, if the outer insertion puncturing needle 21 is pressed into the body, then the outer insertion puncturing needle 21 will move along the guide groove 116 and the tip side portion of the outer insertion puncturing needle 21 will puncture into the body.

If the first rotating portion 122 is in the closed position, then the extraction puncturing needle 30 will be prevented from leaving the guide groove 116 in a direction that is perpendicular to the axial direction. Because the extraction puncturing needle 30 moves along the guide groove 116, it punctures into the body in a proper state, without shifting. The same is true for the second rotating portion 124, where if the second rotating portion 124 is in the closed position, then the outer insertion puncturing needle 21 will be prevented from leaving the guide groove 116 in a direction that is perpendicular to the axial direction. Because the outer insertion puncturing needle 21 moves along the guide groove 116, it punctures into the body in a proper state, without shifting.

With the first rotating portion 122 in the closed position, a locking protrusion 134 interlocks with a locking hole 136 so that a step 140 of the locking protrusion 134 catches on the hole edge of the locking hole 136 to maintain the closed position of the first rotating portion 122, and with the second rotating portion 124 in the closed position, a locking protrusion 130 interlocks with a locking notch 132 so that a step 138 of the locking protrusion 130 catches on the notch edge of the locking notch 132 to maintain the closed position of the second rotating portion 124. Because of this, the closed position of the first rotating portion 122 is maintained, and the closed position of the second rotating portion 124 is maintained, even if the hands are removed from the puncturing needle assisting tool 110. In this way, the state wherein the puncturing needle are placed in the guide grooves 116 (wherein the puncturing needles are set in the puncturing needle assisting tool) is maintained, enabling both hands to be employed in ways other than the work in order to maintain the closed position of the first rotating portion 122, and in ways other than the work in order to maintain the closed position of the second rotating portion 124, such as employed in the puncturing needle puncturing operation. This is particularly useful when puncturing simultaneously with the extraction puncturing needle 30 and the insertion puncturing needle 20.

Note that instead of inserting the puncturing needles one at a time, that is, instead of first positioning the extraction puncturing needle 30 in the first guide groove 116a, closing the first rotating portion 122, and penetrating into the body of the patient, and then placing the outer insertion puncturing needle 21 into the second guide groove 116b, closing the second rotating portion 124, and then penetrating into the body of the patient, instead a plurality of puncturing needles, such as the extraction puncturing needle 30 and the outer insertion puncturing needle 21, may be placed together in the respective corresponding guide grooves 116 (the extraction puncturing needle 30 in the first guide groove 116a and the outer insertion puncturing needle 21 in the secondary groove 116b) and the first rotating portion 122 and the second rotating portion 124 may be closed, making it possible to penetrate, into the body of the patient, either a plurality of puncturing needles simultaneously, or one puncturing needle at a time. Moreover, when positioning the extraction puncturing needle 30 in the guide groove 116, instead of placing the extraction puncturing needle 30 into the guide groove 116 when the first rotating portion 122 is open, it is also possible to place the extraction puncturing needle 30 into the guide groove 116 in a state wherein the first rotating portion 122 is closed. This is also true for the outer insertion puncturing needle 21, where, in positioning the outer insertion puncturing needle 21 in the guide groove 116, instead of placing the outer insertion puncturing needle 21 into the guide groove 116 when the second rotating portion 124 is open, it is also possible to place the outer insertion puncturing needle 21 into the guide groove 116 in a state wherein the second rotating portion 124 is closed.

The position of the lock is not necessarily limited to the design of the first embodiment. However, if the first rotating portion lock is provided at the edge portion that is on the side opposite from the first hinge connecting portion 126 of the first rotating portion 122 and at a portion of the assisting tool main unit 112 corresponding to that edge portion, then the surface opening of the guide groove 116 (the first guide groove 116a) corresponding to the first rotating portion 122 can be closed reliably, and if the second rotating portion lock is provided at the edge portion that is on the side opposite from the second hinge connecting portion 128 of the second rotating portion 124 and at a portion of the assisting tool main unit 112 corresponding to that edge portion, then the surface openings of the guide grooves 116b, 116c, and 116d, corresponding to the second rotating portion 124, can be closed reliably.

While the rotating member need not necessarily be structured from two portions, if the rotating member 114 is structured from the two portions of a first rotating portion 122 and a second rotating portion 124 on the left and right, so that the second rotating portion 124 may assume either an open state or a closed state when the first rotating portion 122 is in the open state, that is, if the surface openings of the second guide grooves 116b, 116c, and 116d can be either open or closed when the surface opening of the first guide groove 116a is in the open state, then if the extraction puncturing needle 30 is first positioned in the first guide groove 116a and the first rotating portion 122 is closed, it is then possible to position the outer insertion puncturing needle 21 in a guide groove 116 by opening and closing the second rotating portion 124 without reopening the first rotating portion 122. This increases operability, such as being able to place individual puncturing needles with certainty.

If the rotating member 114 is structured from two portions, it is not absolutely necessary to have locks on both the first rotating portion 122 and the second rotating portion 124. However, with the first rotating portion 122 in the closed position, a locking protrusion 134 interlocks with a locking hole 136 so that the step 140 of the locking protrusion 134 catches on the hole edge of the locking hole 136 to maintain the closed position of the first rotating portion 122, and with the second rotating portion 124 in the closed position, the locking protrusion 130 interlocks with the locking notch 132 so that the step 138 of the locking protrusion 130 catches on the notch edge of the locking notch 132 to maintain the closed position of the second rotating portion 124, so that after the extraction puncturing needle 30 is first placed in the first guide groove 116a, the closed state of the first rotating portion 122 is maintained enabling the focus to be devoted to placing the insertion puncturing needle 20 next into the second guide groove 116b, 116c, or 116d. Operability is improved to that extent. Note that the step is caught on the edge in interlocking the locking protrusion 134 and the locking hole 136, or in interlocking the locking protrusion 130 and the locking notch 132, enabling interlocking with a sense of confidence.

An interlocking structure wherein the locking protrusion 134 and the locking hole 136 interlock is used in the first rotating portion lock, and an interlocking structure wherein the locking protrusion 130 and the locking notch 132 interlock is used in the second rotating portion lock as well. Structuring the locks from a mutually interlocking locking protrusion and interlocking portion has excellent operability and is simple in terms of manufacturing as well. Using locks comprising a mutually interlocking locking protrusion and interlocking portion for both the first rotating portion lock and the second rotating portion lock is preferred as there will be identical locking operations, increasing the operability to that extent. This is also easy in terms of manufacturing.

The number of guide grooves 116 is not necessarily limited to four. At the least, there is preferably one first guide groove that is closed by the first rotating portion 122, and one second guide groove that is closed by the second rotating portion 124. There may be one first guide groove with more than one second guide groove, or, conversely, more than one first guide groove with one second guide groove, or there may be more than one first guide groove with more than one second guide. However, if there is one first guide groove 116a and more than one second guide groove, such as the three second guide grooves 116b, 116c, and 116d, then the extraction puncturing needle 30 may be placed in the first guide groove 116a and the outer insertion puncturing needle 21 may be placed in any of the second guide grooves 116b, 116c, or 116d, making it possible to select, as appropriate, the spacing between the extraction puncturing needle 30 and the outer insertion puncturing needle 21 depending on the patient, etc. If the second guide groove 116b is selected, then the error will be the smallest. The spacing is sequentially larger for the second guide groove 116b, the second guide groove 116c, and then the [second] guide groove 116d.

Having resisting protrusions 142 provided in the rotating member 114, facing the guide groove 116, so that the resisting protrusions 142 make point contacts with the peripheral surfaces of the extraction puncturing needle 30 and the outer insertion puncturing needle 21 to apply sliding resistance to the extraction puncturing needle 30 and the outer insertion puncturing needle 21, thus preventing the extraction puncturing needle 30 and the outer insertion puncturing needle 21 from falling out in the axial direction by accident, even if the puncturing needle assisting tool 110 is handled with the extraction puncturing needle 30 placed in the guide groove 116 or the outer insertion puncturing needle 21 placed in the guide groove 116. This is effective in a case wherein suturing is to be performed in a plurality of locations so that the unit must wait after being prepared for the next use, or when the puncturing needle assisting tool 110 is placed on the abdomen of the portion on the skin side of the portion to be sutured in the body of the patient after the puncturing needles have already been positioned in the guide grooves 116.

The resistance protrusions 124 are formed to have the same protruding height and shape for each of the guide grooves 116, and so can provide necessary and sufficient sliding resistance in common for the extraction puncturing needle 30 and the outer insertion puncturing needle 21. This is also easy in terms of manufacturing.

The grip portions 144 and 145 increase the operability through enabling the puncturing needle assisting tool 110 to be held away from the guide groove 116 when placing the extraction puncturing needle 30 or when placing the outer insertion puncturing needle 21 in the guide groove 116.

The grip portions 144 and 145 may be structured from a portion on a main unit attachment side of the assisting tool main unit and the rotating member, or, as in the present exemplary embodiment, may be in the form of a protruding piece that protrudes towards the outside from this portion, that is, that extends with a height that is higher than the protruding edge portion 118. This is particularly effective when the top end portion that extends out is held, because this is away from the guide groove 116 not just horizontally, but also in terms of height (vertically). Additionally, rather than the grip portion 144 and the grip portion 145 both protruding, one may instead protrude alone, or in other words, either the grip portion 144 or the grip portion 145 may protrude alone.

Note that by merely providing a stabilizing plate 146 at the bottom end portion of the assisting tool main unit 112, the guide groove 116 is formed continuously in the vertical direction until the bottom end portion of the assisting tool main unit 112. While the guide groove 116 can be of necessary and sufficient length to guide the puncturing needles, the limited effective length of the puncturing needles may be used as the maximum value.

Furthermore, a stabilizing plate 146 at the bottom end part of the assisting tool main unit 112, and when the stabilizing plate 146 comes into contact with the surface of the skin of the patient, the surface of the skin and the guide groove 116 will be perpendicular to each other. Because of this, it is possible for the extraction puncturing needle 30 and the outer insertion puncturing needle 21 to penetrate, at an appropriate angle, the abdominal wall A and the gastric wall B of the patient. Furthermore, because a protruding edge portion 118 is provided at the top end portion of the assisting tool main unit 112 and a guide notch 120 is formed in the protruding edge portion 118, the protruding edge portion 118 serves as a reinforcing portion, increasing the strength of the puncturing needle assisting tool 10.

The protruding edge portion 118 guide notch 120 opens widely in the forward direction, simplifying attachment to the extraction puncturing needle 30 and to the outer insertion puncturing needle 21. This operation is particularly easy when the extraction puncturing needle 30 is inserted between the guide groove 116 and the first rotating portion 122 in a state wherein the first rotating portion 122 is positioned on the front surface side of the assisting tool main unit 112, or when inserting the tip end portion of the outer insertion puncturing needle 21 between the guide groove 116 and the second rotating portion 124 in a state wherein the second rotating portion 124 is on the front surface side of the assisting tool main unit 112.

Additionally, the entirety of the puncturing needle assisting tool 110, including the assisting tool main unit 112 and the rotating member 114, maybe formed integrally out of synthetic resin. A transparent or semitransparent material may also be selected.

An exemplary modification of the first embodiment will be explained next based on FIG. 23.

Figure 23:
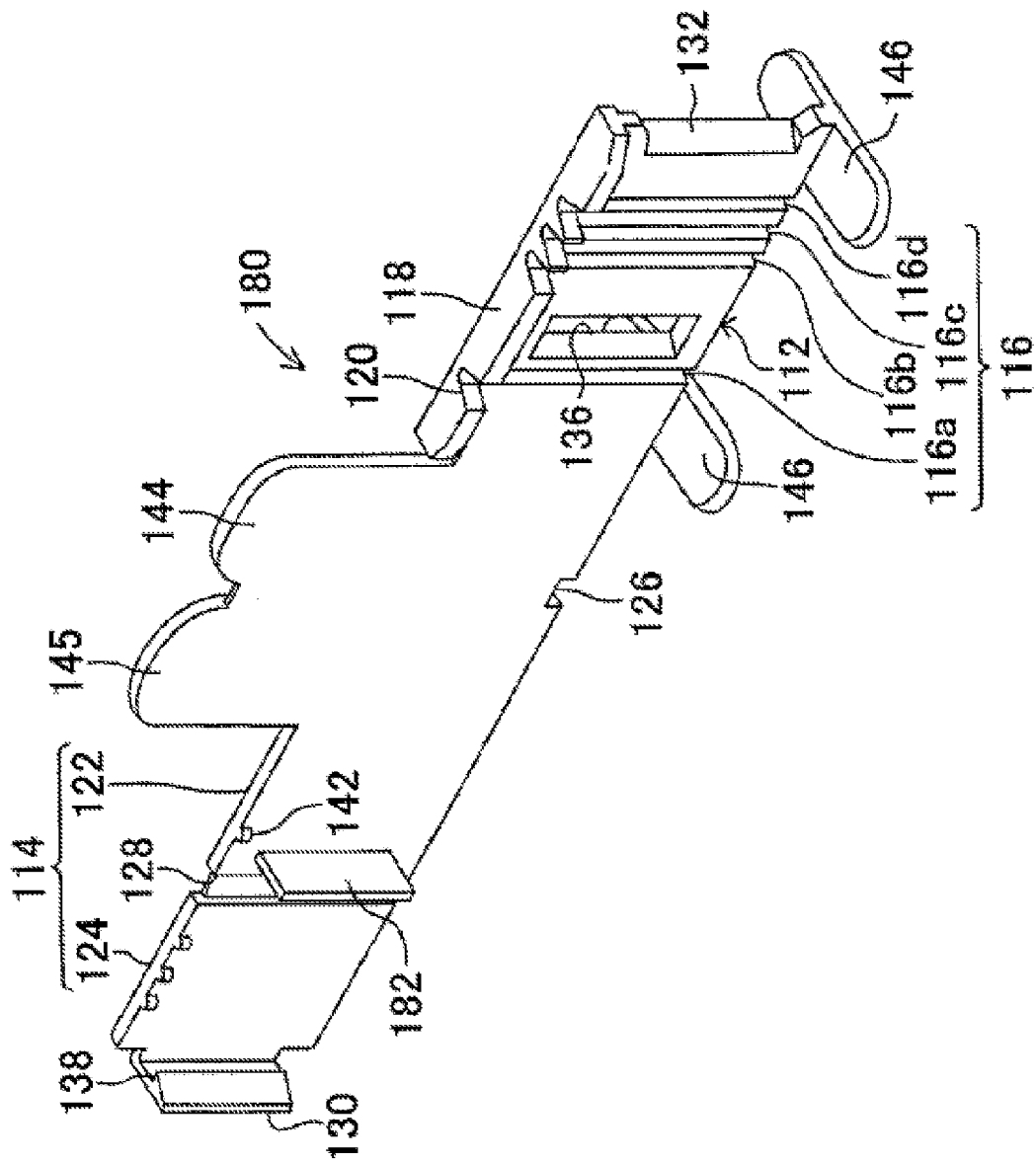
FIG. 23 is a perspective view of a front surface side of an exemplary modification of the puncturing needle assisting tool of the first embodiment of the present invention.

As is illustrated in FIG. 23, the first rotating portion lock of the puncturing needle assisting tool 180 comprises a locking protrusion 182 and a locking hole 136. The locking protrusion 182 is planar with the same thickness over the entirety from the base end to the protrusion tip end, with no step. The locking hole 136 is identical to that in the first embodiment. In the closed position of the first rotating portion 122, the locking protrusion 182 interlocks elastically with the locking hole 136 so as to be able to come apart freely, and when the planar surface of the locking protrusion 182 contacts the hole edge of the locking hole 136, the first rotating portion 122 is maintained in the closed position based on sliding resistance (frictional resistance). This achieves an extremely gentle interlocking force, with superior ease in removing the lock. The rest of the structure, and the effects thereof, are identical to those in the first embodiment.

A second embodiment of the invention will be explained next based on FIG. 24.

Figure 24:
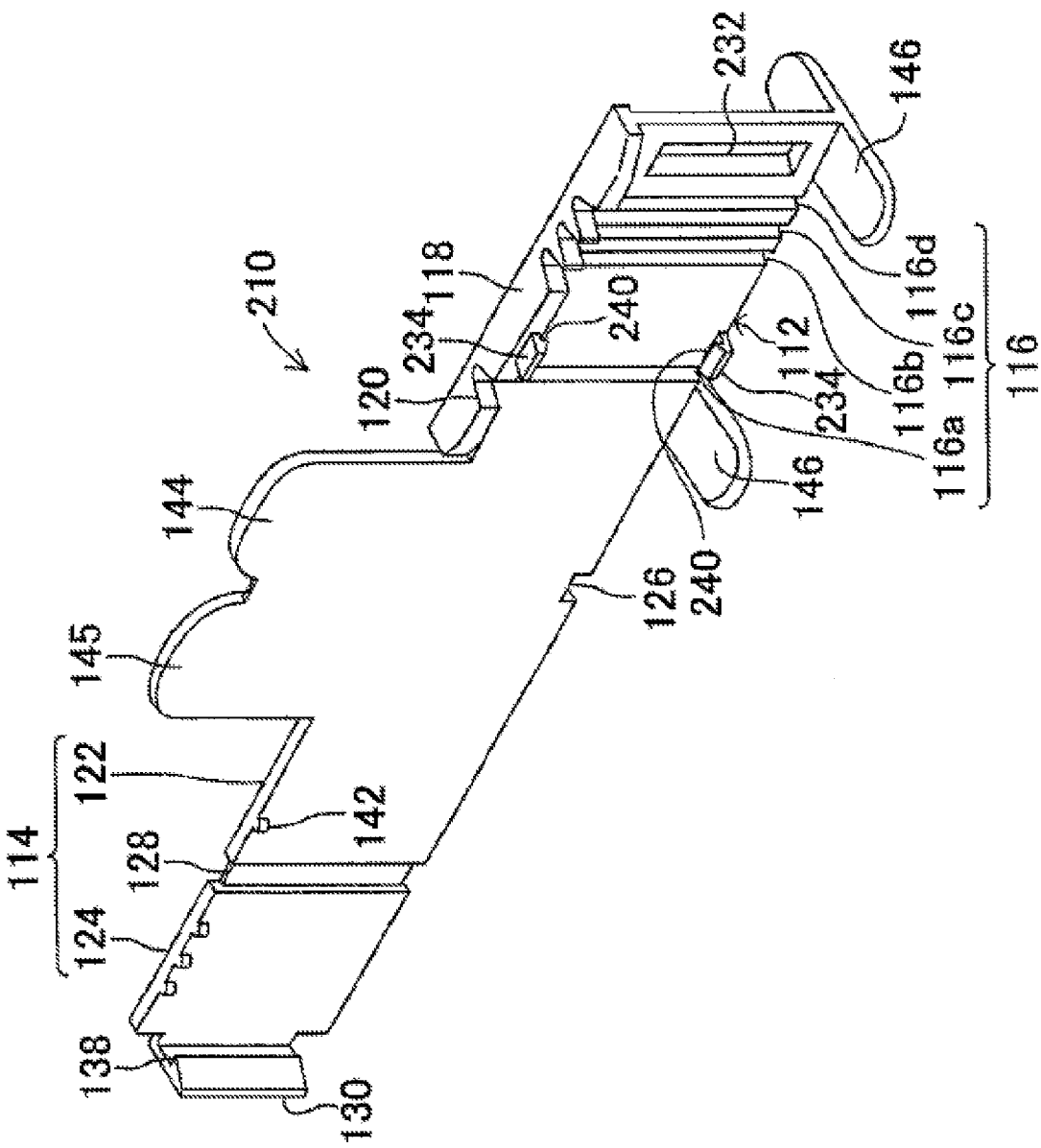
FIG. 24 is a perspective view of a front surface side of the puncturing needle assisting tool according to a second embodiment of the present invention.

The puncturing needle assisting tool 210 of the second embodiment, as illustrated in FIG. 24, replaces the locking protrusion 134 in the first rotating portion lock of the first embodiment with a pair of locking protrusions 234 and 234. The locking protrusions (both labeled 234) are positioned between the first guide groove 116a and the second guide groove 116b, at the bottom edge portions of the protruding edge portion 218 and the assisting tool main unit 112. The locking protrusions 234 are shaped having a step 240 and a wedge shape at the tip end portion, as with the locking protrusion 134 in the first embodiment. At the position of the edge portion on the side that is opposite from the first hinge connecting portion 126 of the first rotating portion 122, a catch is produced wherein the first rotating portion 122 is pinched from above and below between the steps 240 of the locking protrusions 234, and is locked elastically, so as to be removable, at the top and bottom end portions of the locking protrusion 134 and of the first rotating portion 122, to maintain the closed position of the first rotating portion 122. The top and bottom end portions of the first rotating portion 122 function as the interlocking portions.

For the second rotating portion lock, the locking notch 132 of the first embodiment is replaced with a locking hole 232, as the interlocking portion, that is the same as the locking hole 136 in the first embodiment. With the second rotating portion 124 in the closed position, the step 138 of the locking protrusion 130 catches on the hole edge of the locking hole 232, so that the locking protrusion 130 and the locking hole 232 lock elastically so as to be separable, to thereby maintain the closed position of the second rotating portion 124. The rest of the structure, and the effects thereof, are identical to those in the first embodiment.

A third embodiment of the invention will be explained next based on FIG. 25.

Figure 25:
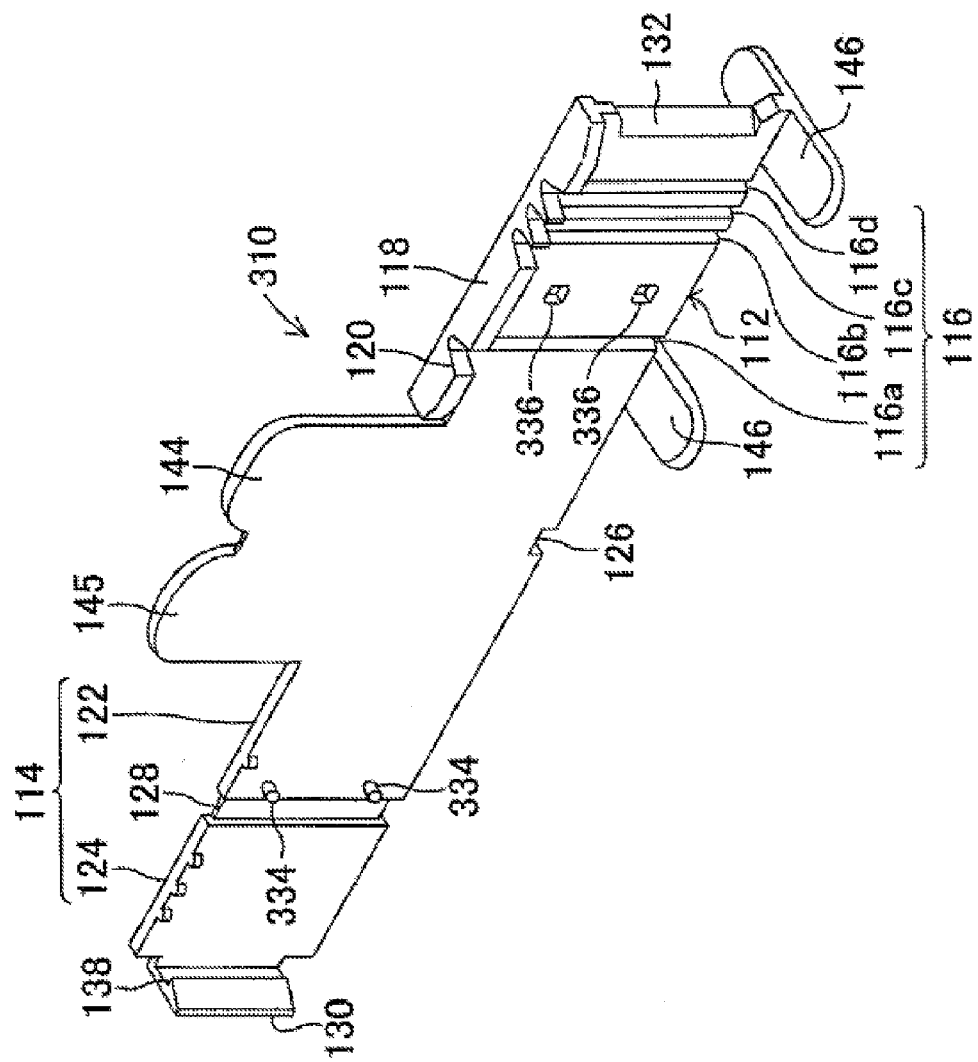
FIG. 25 is a perspective view of a front surface side of the puncturing needle assisting tool according to a third embodiment of the present invention.

In the puncturing needle assisting tool 310 according to the third embodiment, as illustrated in FIG. 25, the first rotating portion lock comprises a pair of columnar locking protrusions (both labeled 334) that are provided protruding with a gap above and below, and a pair of locking holes (both labeled 336), corresponding thereto, as either round or rectangular interlocking portions. The locking protrusions 334 interlock elastically with the locking holes 336 so as to be able to come apart freely, and when the outer peripheral surfaces surface of the locking protrusions 334 contact the outer peripheral surfaces of the locking holes 336, the closed position of the first rotating portion 122 is maintained based on sliding resistance (frictional resistance). As with the modified example of the first embodiment, this achieves an extremely gentle interlocking force, with superior ease in removing the lock. The rest of the structure, and the effects thereof, are identical to those in the first embodiment.

A fourth embodiment will be explained next based on FIG. 26.

Figure 26:
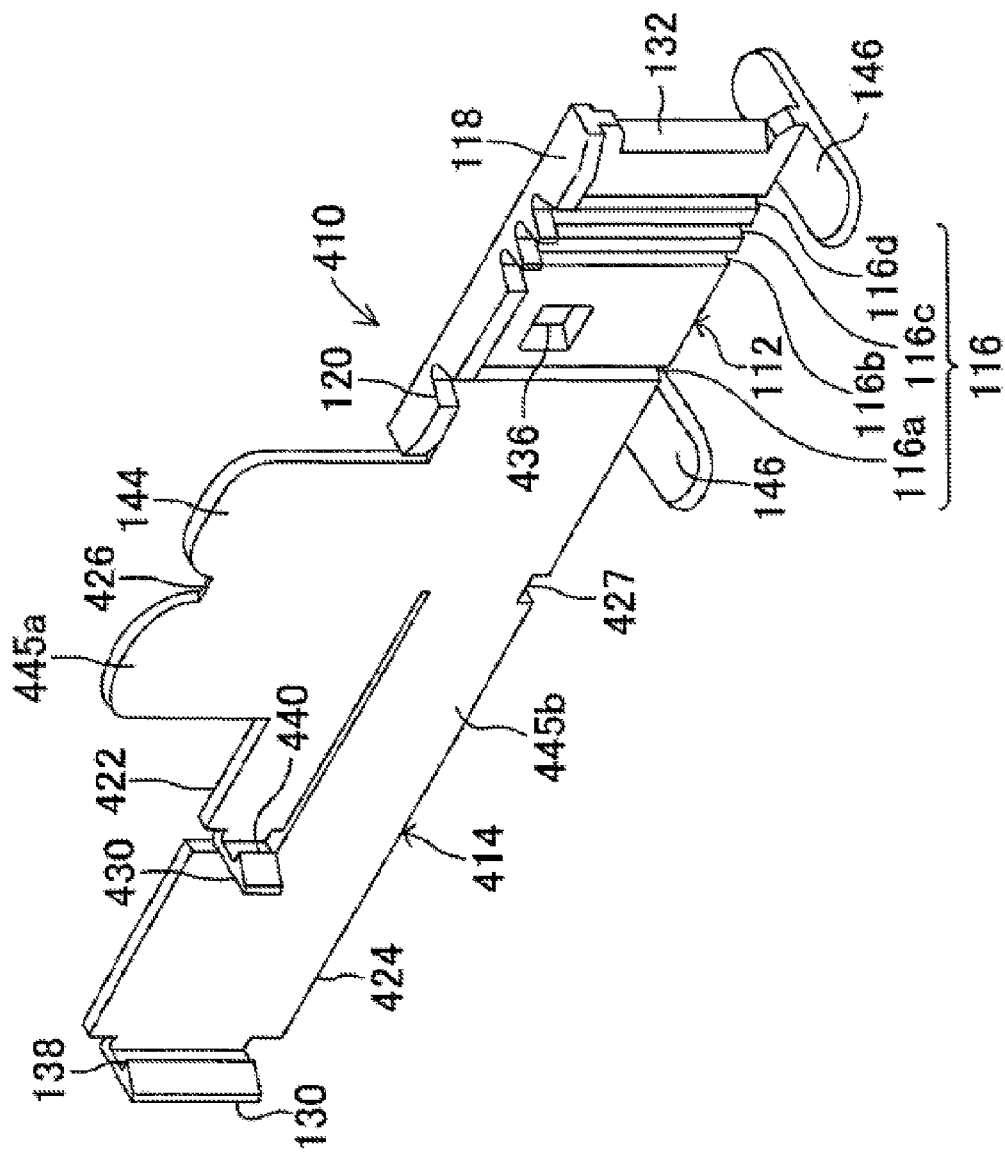
FIG. 26 is a perspective view of a front surface side of the puncturing needle assisting tool according to a fourth embodiment of the present invention.

In the puncturing needle assisting tool 410 according to the fourth embodiment, as illustrated in FIG. 26, not only does the rotating member 414 comprise a first rotating portion 422 and a second rotating portion 424 on the top and the bottom, but also the first rotating portion 422 and the second rotating portion 424 open and close from the same side (the left side). The main unit connection portion comprises a pair of mutually-offset hinge connecting portions 426 and 427. That is, a first hinge connecting portion 426 is positioned on the top side, and a second hinge connecting portion 427 is connected on the bottom side, on the same access as the first hinge connecting portion 426. The first rotating portion 422, positioned on the top side, is attached to the assisting tool main unit 112 by connecting together, through the first hinge connecting portion 426, the edge portions that are essentially parallel to the direction in which the guide grooves 116 extend (the edge portion on the right side of the first rotating portion 422 and the edge portion on the left side of the assisting tool main unit 112). With the first rotating portion 422 in the closed position, the surface opening of the first guide groove 116a will be closed for the portion on the top half of the first guide groove 116a. That is, with the first rotating portion 422 in the closed state, at least a portion of the surface opening of the first guide groove 116a will be closed.

The second rotating portion 424 is attached to the assisting tool main unit 112 by connecting together, through the second hinge connecting portion 427, the edge portions that are essentially parallel to the direction in which the guide grooves 116 extend (the edge portion on the right side of the second rotating portion 424 and the edge portion on the left side of the assisting tool main unit 112). The shape of the second rotating portion 424 is an L shaped standing upward along the edge portion that is on the side opposite of the first hinge connecting portion 426 of the first rotating portion 422, passing under the first rotating portion 422 so as to avoid the first rotating portion 422. With the second rotating portion 424 in the closed position, not only are the surface openings of the second guide grooves 116b, 116c, and 116d closed along the entirety of the portion in the vertical direction of the surface openings of the second guide grooves 116b, 116c, and 116d, but also, at the portion of the first guide groove 116a at the bottom half, the surface opening of the first guide groove 116a is also closed. That is, with the second rotating portion 424 in the closed state, at least the remaining portion of the surface opening that includes portions other than that of the first guide groove 116a will be closed.

The lock comprises a first rotating portion lock and a second rotating portion lock. The first rotating portion lock comprises a locking protrusion 430 and a locking hole 436, as the interlocking portion. A locking protrusion 430 has a length in the vertical direction at the edge portion on the side opposite from a first hinge connecting portion 426 of a first rotating portion of 422 that is short, but is formed similarly to the locking protrusion 130 in the first embodiment. A locking hole 436 is formed in a rectangle, as with the locking hole 136 in the first embodiment, although the link in the vertical direction is short at the portion at the top half of the assisting tool main unit 112, corresponding to the locking protrusion 430, at a position between the first guide groove 116a and the second guide groove 116b. As with the first embodiment, the second rotating portion lock comprises a locking protrusion 130 and a locking notch 132.

The step of the locking protrusion 430 of the first rotating portion 422 catches on the hole edge of the locking hole 436 of the assisting tool main unit 112, so that the locking protrusion 430 and the locking hole 436 lock so as to be separable, to thereby maintain the closed position of the first rotating portion 422. Additionally, the locking protrusion 130 of the second rotating portion 424, and the locking notch 132 of the assisting tool main unit 112 interlock in the same way as in the first embodiment, where the closed position of the second rotating portion 424 is maintained by this interlocking.

The second rotating portion 424 can be in either the open position or the closed position when the first rotating portion 422 is in either the open or the closed position. The opening and closing of the second rotating portion 424 is not affected by the opening or closing of the first rotating portion 422. Looking at the guide grooves 116, this enables the surface openings of the second guide grooves 116b, 116c, and 116d to be opened and closed when the surface opening of the first guide groove 116a is either open or closed. The opening and closing of the surface openings of the second guide grooves 116b, 116c, and 116d is not affected by the opening or closing of the surface opening of the first guide groove 116a. This further increases operability, such as being able to place individual puncturing needles with certainty.

Note that in the present exemplary embodiment, the second rotating portion may be formed in an L shape, the first rotating portion may be formed in the shape of a small square that can be accommodated within the interior angle portion of the first rotating portion (insofar as the shape that protrudes above the group portion is removed), upper portion surface openings of the first guide grooves may be closed by the first rotating portion, and lower portion surface openings of the first guide grooves and second guide grooves, and upper portion surface openings of the second guide grooves, may be closed by the second rotating portion, albeit there is no limitation thereto. For example, the lower portion surface openings of the first guide grooves may be closed by the square first rotating portion, and the upper portion surface openings of the first guide grooves and second guide grooves, and lower portion surface openings of the second guide grooves, may be closed by the L-shaped second rotating portion.

Additionally, the grip portions that are formed on the rotating member 414 are structures into two portions, top and bottom, corresponding, respectively, to the first rotating portion 422 and the second rotating portion 424. Grasping so as to pinch together the grip portion 445*a* of the first rotating portion 422, which is positioned at the top, and the grip portion 144 of the assisting tool main unit 112 enables the first rotating portion 422 to rotate from the open position to the closed position, and grasping so as to pinch together the grip portion 445*b* of the second rotating portion 424 and the grip portion 144 of the assisting tool main unit 112 enables the second rotating portion 424 to rotate from the open position to the closed position.

The rest of the structure, and the effects thereof, are identical to those in the first embodiment.

A fifth embodiment of the invention will be explained next based on FIG. 27.

Figure 27:
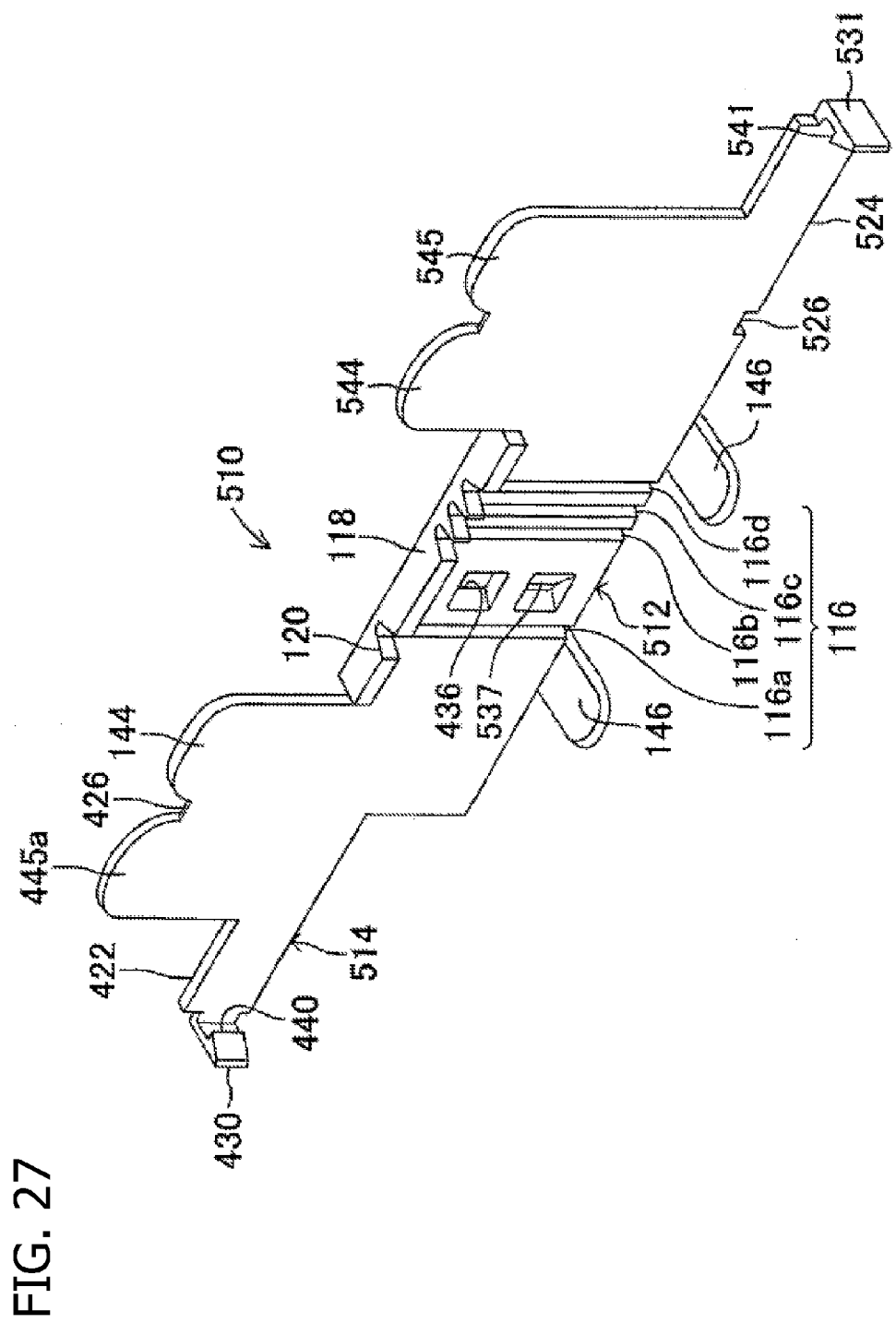
FIG. 27 is a perspective view of a front surface side of the puncturing needle assisting tool according to a fifth embodiment of the present invention.

In the puncturing needle assisting tool 510 according to the fifth embodiment, as illustrated in FIG. 27, a rotating member 514 is structured from two portions at the top end at the bottom, those being a first rotating portion 422 that is identical to that of the fourth embodiment, and a second rotating portion 524 that is different from that of the fourth embodiment. The first rotating portion 422 and the second rotating portion 524 are shaped like gates (opening on both the left and the right). The main unit connection portion comprises a pair of first hinge connecting portions 426 and 526, provided on both edge portions of the assisting tool main unit 512. The first hinge connecting portion 426 is at the edge portion on one side (the left side) of the assisting tool main unit 512, in the same manner as in the fourth embodiment, and the first hinge connecting portion 526 is at the edge portion on the other side (the right side) of the assisting tool main unit 512. The second rotating portion 524 is attached to the assisting tool main unit 512 by connecting together, through a first hinge connecting portion 526, the edge portions that are essentially parallel to the direction in which the guide grooves 116 extend (the edge portion on the left side of the second rotating portion 524 and the edge portion on the right side of the assisting tool main unit 512). With the second rotating portion 524 in the position, the surface openings of the second guide grooves 116*b*, 116*c*, and 116*d* are closed in the bottom half portion of the surface openings of the second guide grooves 116*b*, 116*c*, and 116*d*.

The lock comprises a first rotating portion lock and a second rotating portion lock. As with the fourth embodiment, the first rotating portion lock comprises a locking protrusion 430 and a locking hole 436. The second rotating portion lock comprises a locking protrusion 531 and a locking hole 537, as the interlocking portion. A locking protrusion 531 is formed at the edge portion on the side opposite from a second hinge connecting portion 524 of a first rotating portion of 526, and is formed similarly to the locking protrusion 430. The locking hole 537 is positioned below the locking hole 436 in the portion in the bottom half of the assisting tool main unit 512 corresponding to the locking protrusion 531, in the same manner as the locking hole 436.

Additionally, the locking protrusion 430 of the first rotating portion 422, and the locking hole 436 of the assisting tool main unit 512 interlock, where the closed position of the first rotating portion 422 is maintained by this interlocking in the same way as in the fourth embodiment. On the other hand, the step 541 of the locking protrusion 531 of the second rotating portion 524 catches on the hole edge of the locking hole 537 of the assisting tool main unit 512, so that the locking protrusion 531 of the second rotating portion 524 and the locking hole 537 of the assisting tool main unit 512 lock so as to be separable, to thereby maintain the closed position of the second rotating portion 524.

The second rotating portion 524 can be in either the open position or the closed position when the first rotating portion 422 is in either the open or the closed position. Conversely, this enables the first rotating portion to be in either the open position or the closed position when the second rotating portion is in either the open or the closed position. The opening and closing of the first rotating portion 422 and the opening or closing of the second rotating portion 524 are not affected by each other. Looking at the guide grooves 116, this enables the surface openings of the second guide grooves 116*b*, 116*c*, and 116*d* to be opened and closed when the surface openings of the first guide groove 116*a* are either open or closed, and conversely, this enables the surface openings of the first guide groove 116*a* to be opened and closed when the surface openings of the second guide grooves 116*b*, 116*c*, and 116*d* are either open or closed. The opening and closing of the surface opening of the first guide groove 116*a* is not affected by the opening or closing of the surface openings of the second guide grooves 116*b*, 116*c*, and 116*d*. This further increases operability, such as being able to place individual puncturing needles with certainty.

Moreover, a grip portion 544 is formed identical to the left-side grip portion 144 on the right side of the assisting tool main unit 512 as well (in the portion between the second guide groove 116*d* and the second hinge connecting portion 526), and a grip portion 545 is formed in the portion on the side of the second hinge connecting portion 526 of the second rotating portion 524 as well (in the portion corresponding to between the second guide groove 116*d* and the second hinge connecting portion 526 when the second hinge connecting portion 526 is in the closed position). Grasping so as to pinch together the grip portion 445*a* of the first rotating portion 422 and the grip portion 144 of the left side of assisting tool main unit 512 enables the first rotating portion 422 to rotate from the open position to the closed position, and grasping so as to pinch together the grip portion 545 of the second rotating portion 524 and the grip portion 544 of the right side of the assisting tool main unit 512 enables the second rotating portion to rotate from the open position to the closed position. The rest of the structure, and the effects thereof, are identical to those in the first embodiment and the fourth embodiment.

Note that the puncturing utile assisting tool as set forth in the present invention is not limited to the various embodiments and modified examples set forth above, but rather can be embodied with appropriate variations. For example, although an extraction puncturing needle 30 and an outer insertion puncturing needle 21 for suturing the abdominal wall A and the gastric wall B were used in each of the examples of embodiment and modified examples set forth above, the present invention is not limited thereto, but rather can be used in puncturing needles used for suturing other portions within the body as well.

Moreover, a variety of different locks are possible, where elastic locking, catches, sliding resistance (frictional resistance) and the like can be used, and are not limited to the various examples of embodiment and modified examples set forth above.

Furthermore, the assisting tool main unit 112 and 512 were formed into thin plate shapes in the various examples of embodiment and modified examples set forth above, the assisting tool main unit may instead be formed in a thick plate shape, thereby enabling the stabilizing plate and the protruding edge portion to be eliminated.

An object of the present invention is to provide a puncturing needle assisting tool able to improve the efficiency of the puncturing needle puncturing operations.

One embodiment of the present invention is a puncturing needle assisting tool that is used when inserting a plurality of puncturing needles for securing an internal organ to a skin-side portion using surgical sutures, from the skin-side portion to the internal organ side. The puncturing needle assisting tool comprises an assisting tool main unit with a plurality of parallel guide grooves, wherein the plurality of puncturing needles can be placed in the state enabling movement in the axial direction, are formed in the surface thereof. The tool also comprises a rotating member attached, on an edge portion that is essentially parallel with the direction of the extension of the guide grooves of the assisting tool main unit, so as to be able to rotate, on a main unit attachment portion, from an open position, wherein surface openings of the assisting tool guide grooves are open, to a closed position, wherein the surface openings of the guide grooves are closed, so as to be able to slide on the peripheral surface of the puncturing needles that are positioned in the guide grooves through rotating to the closed side. The tool further comprises a lock, provided on the assisting tool main unit and the rotating member, able to maintain the closed position of the rotating member.

The present invention, with such a structure, enables use as described below when puncturing a plurality of puncturing needles, used for securing an internal organ onto a skin side portion using surgical sutures, into the internal organ side from the skin side portion.

First, the assisting tool main unit is placed on the skin-side portion of the part to be sutured in the body of the patient. With the rotating member in the open position, the puncturing needles are placed inserted into the guide grooves. In a state wherein the rotating member is rotated on the outer surface of the assisting tool main unit to close the surface openings of the guide grooves, if the puncturing needles are pressed against the surface of the body, then the puncturing needles will move along the guide grooves and the tip side portions of the puncturing needles will puncture into the body.

If the rotating member is in the closed position, then the puncturing needles will be prevented from leaving the guide grooves in a direction that is perpendicular to the axial direction. Because the puncturing needles move along the guide grooves, they puncture into the body in a proper state, without shifting.

The rotating member is maintained in the closed position by the interlocking of the lock in the closed position of the rotating member, maintaining the closed position of the rotating member even when the hand is removed from the puncturing needle assisting tool. In this way, the state wherein the puncturing needles are placed in the guide grooves (wherein the puncturing needles are set in the puncturing needle assisting tool) is maintained, enabling both hands to be employed in ways other than the work in order to maintain the closed position of the rotating member, such as in the puncturing needle puncturing operation. This is particularly useful when puncturing simultaneously with a plurality of puncturing needles.

Note that instead of puncturing the body of the patient simultaneously for a plurality of puncturing needles, or individually for each puncturing needle, with the rotating member closed with all of the plurality of puncturing needles in their respective corresponding guide grooves, the puncturing needle may be placed in the guide groove and the rotating member may be closed to puncture into the body of the patient for each individual puncturing needle. Furthermore, in placing the puncturing needles into the guide grooves, rather than inserting the puncturing needles into the guide grooves with the rotating member in the open position, the puncturing needles may be inserted into the guide grooves with the rotating member in the closed position.

In an exemplary embodiment, the rotating member is formed from two portions, a first rotating portion and a second rotating portion. The first rotating portion is attached rotatably by the main unit attachment portion and the second rotating portion is attached rotatably, by an intermediate axis portion, to an edge on the side opposite from the main unit attachment portion of the first rotating portion. The guide grooves comprise first guide grooves and second guide grooves, where the first rotating portion closes the surface openings of the first guide grooves through rotating on the surface side of the assisting tool main unit, and the second rotating portion closes the surface openings of the second guide grooves through rotating on the surface side of the assisting tool main unit.

This enables the second rotating portion to be in either the open position or the closed position when the first rotating portion is in the closed position. That is, this enables the surface openings of the second guide grooves to be opened and closed when the surface openings of the first guide groove are closed. If first one puncturing needle is placed in a first guide groove and the first rotating portion is closed, then next, other puncturing needles can be placed in second guide grooves without reopening the first rotating portion. This increases operability, such as being able to place individual puncturing needles with certainty.

In another exemplary embodiment, the rotating member is formed from two portions, a first rotating portion and a second rotating portion. The main unit attachment portion comprises a pair of main unit attachment portions provided at offset positions on one edge portion of the assisting tool main unit. The first rotating portion and the second rotating portion are attached rotatably, by the pair of main unit attachment portions, to one of the edge portions of the assisting tool main unit in a state wherein they are in mutually offset positions. The guide grooves comprise first guide grooves and second guide grooves, wherein the first rotating portion, by rotating on the surface side of the assisting tool main unit, closes, of the guide grooves, at least the surface openings of a portion of the first guide grooves, and the second rotating portion, by rotating on the surface side of the assisting tool main unit, closes the surface openings of the remaining portion of the guide grooves, including the other portion of the first guide grooves.

This enables the second rotating portion to be in either the open position or the closed position when the first rotating portion is in either the open or the closed position. The opening and closing of the second rotating portion is not affected by the opening or closing of the first rotating portion. Looking at the guide grooves, this enables the surface openings of the second guide grooves to be opened and closed when the surface openings of the first guide groove are either open or closed. The opening and closing of the surface openings of the second guide grooves is not affected by the opening or closing of the surface openings of the first guide grooves. This further increases operability, such as being able to place individual puncturing needles with certainty.

In this case, the second rotating portion may be formed in an L shape, the first rotating portion may be formed in the shape of a small square that can be accommodated within the interior angle portion of the first rotating portion, upper portion surface openings of the first guide grooves may be closed by the first rotating portion, and lower portion surface openings of the first guide grooves and second guide grooves, and upper portion surface openings of the second guide grooves, may be closed by the second rotating portion. Additionally, the lower portion surface openings of the first guide grooves may be closed by the square first rotating portion, and the upper portion surface openings of the first guide grooves and second guide grooves, and lower portion surface openings of the second guide grooves, may be closed by the L-shaped second rotating portion.

In another exemplary embodiment, the rotating member is formed from two portions, a first rotating portion and a second rotating portion. The main unit attachment portion comprises a pair of main unit attachment portions equipped respectively on the edge portions on both sides of the assisting tool main unit. The first rotating attachment portion is attached by one of the main unit attachment portions to one edge of the assisting tool main unit and the second rotating attachment portion is attached by the other main unit attachment portion to the other edge portion of the assisting tool main unit. The guide grooves comprise first guide grooves and second guide grooves, where the first rotating portion closes the surface openings of the first guide grooves through rotating on the surface side of the assisting tool main unit, and the second rotating portion closes the surface openings of the second guide grooves through rotating on the surface side of the assisting tool main unit.

This enables the second rotating portion to be in either the open position or the closed position when the first rotating portion is in either the open or the closed position. Conversely, this enables the first rotating portion to be in either the open position or the closed position when the second rotating portion is in either the open or the closed position. The opening and closing of the first rotating portion and the opening or closing of the second rotating portion are not affected by each other. Looking at the guide grooves, this enables the surface openings of the second guide grooves to be opened and closed when the surface openings of the first guide groove are either open or closed, and conversely, this enables the surface openings of the first guide grooves to be opened and closed when the surface openings of the second guide groove are either open or closed. The opening and closing of the surface openings of the second guide grooves and the opening or closing of the surface openings of the first guide grooves are not affected by each other. This further increases operability, such as being able to place puncturing needles with certainty for each individual puncturing needle.

In another exemplary embodiment, the lock comprises a first rotating portion lock provided on the edge portion on the side opposite of the main unit attachment portion of the first rotating portion and on the portion of the assisting tool main unit corresponding to that edge portion. The lock also comprises a second rotating portion lock provided on the edge portion on the side opposite of the intermediate axis portion of the second rotating portion and on the portion of the assisting tool main unit corresponding to that edge portion.

This enables the closed position of the first rotating portion to be maintained by the first rotating portion lock, and enables the closed position of the second rotating portion to be maintained by the second rotating portion lock. After one puncturing needle has been placed in a first guide groove, it is possible to apply the effort of maintaining the closed position of the first rotating portion instead to, for example, placing other puncturing needles in the second guide grooves. Operability is improved to that extent.

In another exemplary embodiment, the lock comprises a first rotating portion lock provided on the edge portion on the side opposite of the main unit attachment portion of the first rotating portion and on the portion of the assisting tool main unit corresponding to that edge portion. The lock also comprises a second rotating portion lock provided on the edge portion on the side opposite of the main unit attachment portion of the second rotating portion and on the portion of the assisting tool main unit corresponding to that edge portion.

This also enables the closed position of the first rotating portion to be maintained by the first rotating portion lock, and enables the closed position of the second rotating portion to be maintained by the second rotating portion lock. After one puncturing needle has been placed in a first guide groove, it is possible to apply the effort of maintaining the closed position of the first rotating portion instead to, for example, placing other puncturing needles in the second guide grooves. Operability is improved to that extent.

In another exemplary embodiment, the lock comprises a mutually interlocking locking protrusion and interlocking portion. Structuring the lock from a mutually interlocking locking protrusion and interlocking portion in this way has excellent operability and is simple in terms of manufacturing as well. Using a lock comprising a mutually interlocking locking protrusion and interlocking portion for both the first rotating portion lock and the second rotating portion lock is preferred as there will be identical locking operations, increasing the operability to that extent. This is also easy in terms of manufacturing.

In another exemplary embodiment, the first guide groove is a single groove, and the second guide groove is two or more grooves. Doing so enables the placement of one puncturing needle in the first guide groove and enables the appropriate selection of spacing of the other puncturing needles from the one puncturing needle through the use of any of the two or more second guide grooves for the other puncturing needle, when using two puncturing needles, namely the first puncturing needle and in other puncturing needle.

In another exemplary embodiment, a resisting protrusion for providing a sliding resistance on the peripheral surface of a puncturing needle disposed in the guide groove, is provided on the rotating member so as to face the guide groove in the closed position of the rotating member. Doing so enables the prevention of the puncturing needle from falling out in the axial direction in a case such as when the equipment is waiting during preparations for the next use, or a case such as when, after a puncturing needle has already been placed in a guide groove, the puncturing needle assisting tool is placed on the skin-side portion of the portion to be sutured on the body of the patient, even when the puncturing needle assisting tool is handled with a needle placed in a guide groove. Note that the resistance of the resistance protrusion can be of the degree so as to prevent the puncturing needle from falling under its own weight.

Furthermore, the resistance protrusion may be formed as a single protrusion for each*, and may provide the necessary and adequate sliding resistance for all puncturing needles thereby. This is also easy in terms of manufacturing.

In another exemplary embodiment, when the rotating member is in the closed position, a grip portion that is positioned between the main unit attachment portion and the guide groove that is nearest to the main unit attachment portion is formed at the assisting tool main unit and the rotating member. This increases the operability when placing a puncturing needle in a guide groove, through enabling the puncturing needle assisting tool to be held other than by the guide groove when placing a puncturing needle into a guide groove.

The grip portion in this case may be formed by a portion on the main unit attachment side of the assisting tool main unit and the rotating member, and may be formed as a protruding piece that protrudes towards the outside from that portion.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A puncturing needle assisting tool for use with a plurality of puncturing needles, said assisting tool comprising:
   an assisting tool main unit comprising a main unit attachment portion and a plurality of parallel guide grooves on the main unit attachment portion, wherein the plurality of parallel guide grooves comprise at least one first guide groove and second guide grooves on the main unit attachment portion;
   a first rotating portion and a second rotating portion, the first rotating portion having a first edge attached to the main unit attachment portion by a first hinge and rotatable onto the main unit attachment portion to cover at least a portion of said first guide groove, the second rotating portion attached to the first rotating portion at a second edge thereof opposite from the first edge and rotatable onto the main unit attachment portion to cover at least a portion of at least one of said second guide grooves;
   a first lock comprising a first locking protrusion disposed on the first rotating portion, and a locking hole disposed on the main unit attachment portion, the first locking protrusion engageable with the locking hole; and
   a second lock comprising a second locking protrusion disposed on the second rotating portion, and a locking notch disposed on the main unit attachment portion, the second locking protrusion engageable with the locking notch.

2. The puncturing needle assisting tool of claim 1, wherein said at least one first guide groove comprises a single first guide groove.

3. The assisting tool of claim 2, wherein a spacing between said single first guide groove and an adjacent second guide groove is greater than a spacing between two adjacent second guide grooves.

4. The puncturing needle assisting tool of claim 1 comprising a resisting protrusion for providing a sliding resistance on the peripheral surface of a puncturing needle disposed in the guide groove, said resisting protrusion provided on at least one of the first rotating portion and the second rotating portion.

5. The puncturing tool of claim 1 further comprising a grip portion at the assisting tool main unit.

6. The assisting tool of claim 1, further comprising a stabilizing plate disposed on the main unit attachment portion.

7. The assisting tool of claim 1, further comprising a protruding edge portion on an edge portion of the main unit attachment portion, the protruding edge portion having a plurality of guide notches, the plurality of guide notches disposed to align with the plurality of guide grooves.

* * * * *